United States Patent
Imam et al.

(10) Patent No.: US 12,404,530 B2
(45) Date of Patent: *Sep. 2, 2025

(54) METHODS FOR PRODUCING A COMPOSITION CONTAINING LIPIDS FROM RECOMBINANT ALGAE HAVING HIGH LIPID PRODUCTIVITY

(71) Applicant: Viridos, Inc., La Jolla, CA (US)

(72) Inventors: Saheed Imam, La Jolla, CA (US); Eric R. Moellering, La Jolla, CA (US); Luke Peach, La Jolla, CA (US); Wiilliam F. Lambert, La Jolla, CA (US); Kathleen Kwok, La Jolla, CA (US)

(73) Assignee: Viridos, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/632,080

(22) Filed: Apr. 10, 2024

(65) Prior Publication Data

US 2024/0247290 A1     Jul. 25, 2024

Related U.S. Application Data

(63) Continuation of application No. 17/519,383, filed on Nov. 4, 2021, now Pat. No. 11,976,315.

(60) Provisional application No. 63/110,301, filed on Nov. 5, 2020.

(51) Int. Cl.
    *C12P 7/64*           (2022.01)
    *C07K 14/405*     (2006.01)
    *C12N 1/12*         (2006.01)

(52) U.S. Cl.
CPC .............. *C12P 7/64* (2013.01); *C07K 14/405* (2013.01); *C12N 1/125* (2021.05)

(58) Field of Classification Search
None
See application file for complete search history.

(56) References Cited

U.S. PATENT DOCUMENTS

| | | | |
|---|---|---|---|
| 11,976,315 B2 * | 5/2024 | Imam | C12N 1/125 |
| 2004/0006797 A1 | 1/2004 | Shi et al. | |
| 2016/0273061 A1 | 9/2016 | Hayakawa et al. | |
| 2018/0371401 A1 | 12/2018 | Harayama et al. | |

FOREIGN PATENT DOCUMENTS

WO    WO 2021/126987 A1    6/2021

OTHER PUBLICATIONS

Chen et al., "Transparent Testa GLABRA1 Regulates the Accumulation of Seed Storage Reserves in Arabidopsis", Plant Physiology, Sep. 2015, 169(1): 391-402.
EP Extended Search Report in European Application No. 21890079.3, dated Sep. 13, 2024, 11 pages.
Gachomo et al., "GIGANTUS1 (GTS1), a member of Transducin/WD40 protein superfamily, controls seed germination, growth and biomass accumulation through ribosome-biogenesis protein interactions in *Arabidopsis thaliana*", BMC Plant Biology, Jan. 2014, 14(1): 37, 17 pages.
Chica et al., Curr. Opin. Biotechnol. (2005), 16(4):378-384.
PCT International Search Report and Written Opinion in International Application No. PCT/US2021/058092 date Mar. 25, 2022, 11 pages.
Singh et al., Curr. Protein Pept. Sci. (2017), 18:1-11.

* cited by examiner

*Primary Examiner* — Christian L Fronda
(74) *Attorney, Agent, or Firm* — DLA Piper LLP (US)

(57) ABSTRACT

The invention provides recombinant algal mutants that have a genetic modification to a gene or nucleic acid sequence encoding a WD40 repeat containing protein or domain. The genetic modification of one or more nucleic acid sequences encoding a WD40 repeat containing protein or domain results in a mutant organism with increased lipid productivity and/or higher biomass productivity (as measured by total organic carbon). The genetic modification can be a gene attenuation or functional deletion. The lipid products of these mutants can be utilized as biofuels or for other specialty chemical products. Methods of making and using the recombinant algal mutants and methods of producing lipids are also disclosed.

18 Claims, 8 Drawing Sheets

Figure 1A:
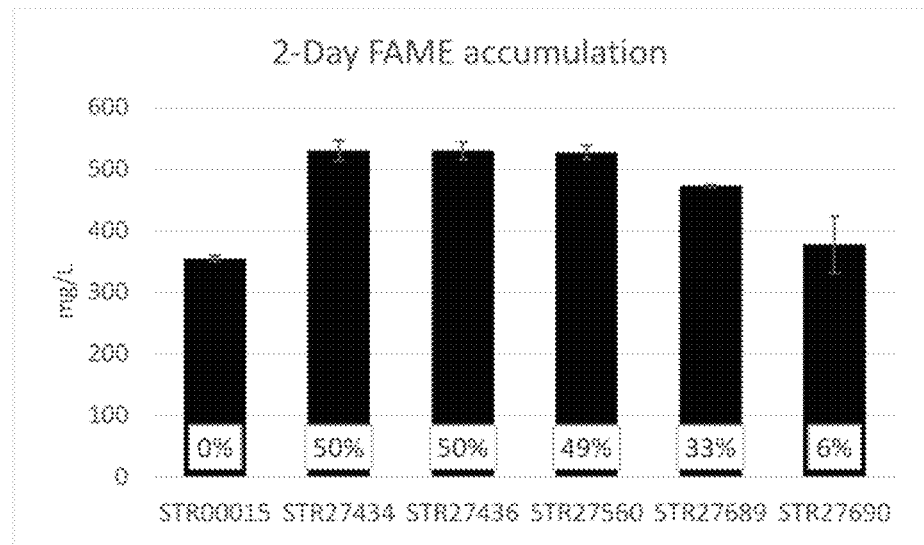

Specification includes a Sequence Listing.

FIG. 5

```
                        SEQUENCE LISTING

Sequence total quantity: 26
SEQ ID NO: 1            moltype = AA  length = 340
FEATURE                 Location/Qualifiers
REGION                  1..340
                        note = misc_feature - WD40 repeat protein, 3EUKT2027500
source                  1..340
                        mol_type = protein
                        organism = Oocystis sp.
SEQUENCE: 1
MAEPDANGAS DGKRAEIYTY EFPNLVYSMN WTSRRDKKFR LAVGSFIEDY NNVVNIISLD   60
EEQGKFVCDP SLTFKHPYPP TKVMFVPDRE GTRPDLLATT GDYLRVWKIG EDGVTLQKLL  120
NDNKNSEFCA PLTSFDWNET DPKRLGTSSI DTTCTIWDIE KGVVDTQLIA HDKEVYDIAW  180
GGVGVFASVS ADGSVRVFDL RDKEHSTIIY ETPSPETPLL RLGWNKQDPR YMATIVMDSN  240
RVVVLDIRVP TVPVAELQRH QACANALAWA PHSSCHICTA GDDAQALIWD LSAVSKEGDS  300
GLDPILAYNA GQEVNQLQWS STQPDWVAVC FGNKAQILRV                       340

SEQ ID NO: 2            moltype = AA  length = 335
FEATURE                 Location/Qualifiers
REGION                  1..335
                        note = misc_feature - WD40 repeat protein
source                  1..335
                        mol_type = protein
                        organism = Coccomyxa sp.
                        note = Coccomyxa subellipsoidea
SEQUENCE: 2
MDGRLNDRRA EIYTYDSENI VYGLSWSNRR DKKFRLAVGS FIEEYDNYVE IITLDDATCK   60
FTSDAQLAFQ HPYPPTKIMF MPDKEGAQPD LLATTGDYLR IWQLKEDGTQ LVKLLNNNKN  120
SEFCAPLTSF DWNETDLNRL GTSSIDTTCT IWDIEKGVVD TQLIAHDKEV YDIAWGGVGV  180
FASVSADGSV RVFDLRDKEH STIIYDSPQP DTPLLRLGWN KQDPRYMATV LMDSTKVVIL  240
DIRYPTLPVA ELQRHQAPVN AVAWAPHSSC HICSAGDDAQ ALIWDLSSMS RPMDQTLDPI  300
LAYSAGAEVN QLQWSTTQPD WVAICFANKT QILRV                            335

SEQ ID NO: 3            moltype = AA  length = 359
FEATURE                 Location/Qualifiers
REGION                  1..359
                        note = misc_feature - WD40 repeat protein
source                  1..359
                        mol_type = protein
                        organism = Chlamydomonas reinhardtii
SEQUENCE: 3
MSASDKRERQ EVYTYVAPDP VYAMNWSVRR DKRFRLGVAS FREDVTNYVD IVSLDDESDE   60
LRADPGLRFP HDYPATKLMW MPDREGCRPD LLATTGEALR IWRVCDGSEG EESGSGPGGR  120
GVQLRSLLNN NKQSEFSAPL TSFDWNEADP KRLGTSSIDT TCTIWDIEKG EVDTQLIAHD  180
REVYDIAWGG LGVFATVSAD GSVRVFDLRD KEHSTIIYES PQPDTPLLRL GWNRQDPRYM  240
ATILQDSPKV VILDIRYPTL PVAELCRHQA PVNALAWAPH SAQHICTAGD DSQALIWDVS  300
AVGGGNNANA AAGGGASDVS LDPILAYGAA SEVNQLQWSS AQPDWVAICF GNKTQILRV   359

SEQ ID NO: 4            moltype = AA  length = 351
FEATURE                 Location/Qualifiers
REGION                  1..351
                        note = misc_feature - WD40 repeat protein
source                  1..351
                        mol_type = protein
                        organism = Volvox sp.
                        note = Volvox carteri
SEQUENCE: 4
MSNSDKRAEI YTYVAQDPVY AMNWSVRRDR RFRLAVGSFR EDVTNYVEII SLDDDAAELR   60
SDPSLRFHHD YPATKLMWLP DREGCRPDLL ATTGEALRIW RVLDPDSVAG DGEDLRALLN  120
NNKQSEFSAP LTSFDWNEAD PKRLGTSSID TTCTIWDIEK GEVDTQLIAH DREVYDIAWG  180
GLGVFATVSA DGSVRVFDLR DKEHSTIIYE SPQPDTPLLR LGWNRQDPRY MATILMDSPK  240
VVILDIRYPT LPVAELHRHQ APVNALAWAP HSAQHICTAG DDSQALIWDV SAVGSGGGQP  300
GALGGGTAGD VSLDPILAYG AQSEVNQLQW SSAQPDWVAI CFANKTQILR V           351

SEQ ID NO: 5            moltype = AA  length = 341
FEATURE                 Location/Qualifiers
```

```
REGION                      1..341
                            note = misc_feature - WD40 repeat protein
source                      1..341
                            mol_type = protein
                            organism = Chlorella protothecoides
                            note = Auxenochlorella protothecoides
SEQUENCE: 5
MSGPSGDKRA EIYTHESADP IYALNWSVRT DKPFRLATGS YVEDQNNHID IIVLDEAREQ    60
FQADPRLSFV HPFPATKLMF LPVKDPNQPD LLATTSDFLR IWSISEDGVA LEKLLNNTKT   120
SEYCEPITSF DWNHLEPRRL GTASLDATCT VWDIERGCVD TQLIAHDGEV YDLAWGGATM   180
FASVSADASV RVFDLRDRDH STITYESRGG EALVRLGWNR ADPRFMAVLA AGSAEVVVLD   240
VRRPAAPLAR LARHTAPANV LAWAPHSACH LCSAGDDGAA LIWDVGALGG GGGPGGAAQD   300
PGLDPILAYN AGAEVAALQW SAAQPDWVAI AFGNNAQVLR V                      341

SEQ ID NO: 6                moltype = AA  length = 351
FEATURE                     Location/Qualifiers
REGION                      1..351
                            note = misc_feature - WD40 repeat protein
source                      1..351
                            mol_type = protein
                            organism = Chlorella sorokiniana
SEQUENCE: 6
MQQQGEGRAE IYTYESPHLV YGAGWSVRPD KPFRLALGSF IEDYANRVEI VQLDEGRGVI    60
RSNPALGFQH PYPPTKVGFI PDKDGTRPDL LATSGDFLRL WRIHDEPGSN QHVRLEKLLN   120
NNKGGEFSAP LTSFDWNELD PRRIGTASID TTCTVWDVER GVVDTQLIAH DKEVYDIAWG   180
GVGIFASVSA DGSVRVFDLR DKEHSTIIYE SPQPSTPLLR LSWNKQDPRY IAAFAMDSSK   240
VLVLDIRYPT LPVAQLQRHQ ASVNAVCWAP HSAVHLCSAG DDCQALIWDL ALSGAMGGQQ   300
QDGTAAAAAA GGLDPILAYN AGTEINQLQW SASQPDWVAI CFGNKAQILR V            351

SEQ ID NO: 7                moltype = AA  length = 355
FEATURE                     Location/Qualifiers
REGION                      1..355
                            note = misc_feature - WD40 repeat protein
source                      1..355
                            mol_type = protein
                            organism = Chlorella sp.
                            note = Chlorella variabilis
SEQUENCE: 7
MQDQQQQGEG RAEIYTYSSS ASVYACGFSS RPDKPFRLAV GSFIDDYANK VEIIQLDEAA    60
GVVRNNPALT FQHPYPPTKV AFIPDKSGTR PDLLATSGDF LRLWRVSDEP GAQQGVRLEK   120
LLNNNKGGDF AAPLTSFDWN ELDPRRVGTA SIDTTCTVWD VERGVVDTQL IAHDKEVYDI   180
AWGGVGIFAS VSADGSVRVF DLRDKEHSTI IYESPQPDTP LLRLSWNKQD PRYIAVLAMD   240
SPRVTVLDIR YPTLPVAELQ RHQAGVNAIC WAPHSATHLC SAGDDSQALI WDLGLLGTLG   300
QQPEGGPPGA AAAGGGLDPI LAYNAGAEVN QLQWSPAQPD WVAICFGNKT QLLRV        355

SEQ ID NO: 8                moltype = AA  length = 334
FEATURE                     Location/Qualifiers
REGION                      1..334
                            note = misc_feature - WD40 repeat protein
source                      1..334
                            mol_type = protein
                            organism = unidentified
                            note = Parachlorella sp.
SEQUENCE: 8
MQRAEIHTYE SPTLVYALNW SVRPDKPFRL AIGSYIEDYN NRVEIVTLGE DGNGMRPSPR    60
HTFQHPYPPT KLQFVPDPDG SRPDLLASSG DFLRLWRITE DGVSLEKLLN NNKASEFCAP   120
LTSFDWNEND PKRVGTASID TTCTVWDIEK GVVDTQLIAH DKEVYDIAWG GVGVFASVSA   180
DGSVRVFDLR DKEHSTIIYE SPQPDTPLLR LAWNKQDPRY MATTALNSSA IVVLDIRFPT   240
VPVVELSKHQ AACNAVAWAP QSANHICSAG DDCQALIWDL STLGEGGAGQ AGSPPLDPIL   300
SYMAGAEVNQ LQWSASHPDW VAICFGNKTQ ILRV                               334

SEQ ID NO: 9                moltype = AA  length = 337
FEATURE                     Location/Qualifiers
REGION                      1..337
                            note = misc_feature - WD40 repeat protein
source                      1..337
                            mol_type = protein
                            organism = unidentified
                            note = Picochlorum celeri
SEQUENCE: 9
MEHPPAPNIL TYDSSSIVFA LDWSSRQDKG VRVAVGSFVE GVSNTVEILR VTPAGLIVDD    60
KETFGIEYPA TQVGFIPDRF CNKPDLLATS GDAVRLWKIS DAGTTLELVL NDPKNTSKNF   120
SAVTCFDWSE INVKVLAAGS SAGRLLLWDT ESGRLQGTMV GHEDEILDCQ WAANDVIVSS   180
SGDGSIRMYD LRDKDHCTVL YETPRRTPVP RFCWNKLDPR HLAFSIEKSR LVSVLDVRFP   240
TEPVILLDGH MGNCTALGWS PHREEYLCSV GDDCHALIWD VGKVNSEEDS KPNREAVDAS   300
PILAYNAQAE INAMAWNPID PDWIAICARN RTQVLRI                            337

SEQ ID NO: 10               moltype = AA  length = 412
FEATURE                     Location/Qualifiers
```

```
REGION                    1..412
                          note = misc_feature - WD40 repeat protein
source                    1..412
                          mol_type = protein
                          organism = Tetraselmis sp.
SEQUENCE: 10
MPTSDATQAH EHHHTLAATP TQQANNAAPL ADRFTLGLLA MASGPEDRGA GAAGAAPHQR   60
GDSNGKAVTD KRGEIYTYEA PYPVYGMNWS VLLQVREDMK FRLAVGSFVE DVENAVELIR  120
LNEETGKFES NPAHKFVHPY PPTKIMFIPD RDCSRPDLLA TTGDYLRLWR VEEDGVTLHK  180
LLTNNKNSEF CAPLTSFDWN EADPRQLGTS SIDTTCTIWD IERGVVDTQL IAHDKEVYDI  240
AWGGQGVFAS VSADGSVRVF DLRDKDHSTI IYESGMPEIP LLRLGWNKQD PRYMATILMD  300
SSKVVVLDIR YPTMPVAELE AHHKPVNALA WAPQSSSHIC TAGDDAQALI WNLAPMGTQG  360
PMGGAAPAVL GADLDPILAY NAGEEINQLQ WSSTQSDWVG ISFGNKIQIL RI          412

SEQ ID NO: 11             moltype = AA   length = 332
FEATURE                   Location/Qualifiers
REGION                    1..332
                          note = misc_feature - WD40 repeat protein
source                    1..332
                          mol_type = protein
                          organism = unidentified
                          note = Ostreococcus lucimarinus
SEQUENCE: 11
MNAEKRAEIY TYEAPWMIYA CNWSVRQDKR FRLALGSFVE EYSNKVEIIT LDEETGEFPK   60
EAQCSFTHPY PCTKILFIPD KECTKEDLLA TTGDYLRIWQ VQDDNTVQMK SLLNNNKSSE  120
FCAPLTSFDW NETKLQRVGT SSIDTTCTIW DIERECVDTQ LIAHDKEVYD IAWGGPEVFA  180
SVSADGSVRV FDLRDKDHST IIYESQTPDT PLLRLGWNKQ DPRYMATICM DSPVIILDIR  240
FPTLPVAELQ SHRASVNTLA WAPHSSSHMC TAGDDSQALI WDLSSMNQPP EGGLDPILAY  300
SAGAEINQLQ WSASQPDWIS IAFRNSLQIL RV                                332

SEQ ID NO: 12             moltype = AA   length = 336
FEATURE                   Location/Qualifiers
REGION                    1..336
                          note = misc_feature - WD40 repeat protein
source                    1..336
                          mol_type = protein
                          organism = Micromonas sp.
                          note = Micromonas commoda
SEQUENCE: 12
MAAMGSGQSG AEIYTYEAPW LVYAMNWSVR QDKRFRLALG SFVEEYSNKV EIITLDEQRR   60
EFPAEPTHRF DHPYPCTKIM FVPDAEGTSE DLLATSGDYL RVWRIGDDGV HLRSLLNNNK  120
NSDFCAPLTS FDWSTTNLAR VGTSSLDTTC TIWDLEKETV DSQLIAHDKE VYDIAWGGPE  180
VFASVSADGS VRVFDLRKD HSTIVYESPT PDTPLLRLGW NKQNPRYMAT MEMDSAKVVV  240
LDIRVPALPV AELKKHRAAV NTLAWAPHSS RNICTAGDDA QALIWDLSSV AQPGEDGMDP  300
MLAYNAGAEI SQLQWSATQT DWIAIAFGKN LQVLHV                            336

SEQ ID NO: 13             moltype = AA   length = 346
FEATURE                   Location/Qualifiers
REGION                    1..346
                          note = misc_feature - WD40 repeat protein
source                    1..346
                          mol_type = protein
                          organism = Arabidopsis sp.
SEQUENCE: 13
MGTSSDPIQD GSDEQQKRSE IYTYEAPWHI YAMNWSVRRD KKYRLAITSL LEQYPNRVEI   60
VQLDESNGEI RSDPNLSFEH PYPPTKTIFI PDKECQRPDL LATSSDFLRL WRIADDHSRV  120
ELKSCLNSNK NSEFCGPLTS FDWNEAEPRR IGTSSTDTTC TIWDIEREAV DTQLIAHDKE  180
VFDIAWGGVG VFASVSADGS VRVFDLRDKE HSTIIYESSE PDTPLVRLGW NKQDPRYMAT  240
IIMDSAKVVV LDIRFPALPV VELQRHQASV NAIAWAPHSS CHICTAGDDS QALIWDISSM  300
GQHVEGGLDP ILAYTAGAEI EQLQWSSSQP DWVAIAFSTK LQILRV                 346

SEQ ID NO: 14             moltype = DNA   length = 12
FEATURE                   Location/Qualifiers
misc_feature              1..12
                          note = partial sequence of WD40 repeat protein
source                    1..12
                          mol_type = unassigned DNA
                          organism = Oocystis sp.
SEQUENCE: 14
agactcgcac cg                                                       12

SEQ ID NO: 15             moltype = DNA   length = 1643
FEATURE                   Location/Qualifiers
misc_feature              1..1643
                          note = WD40 repeat protein, 3EUKG2027500, encodes SEQ ID
                            NO: 1
source                    1..1643
                          mol_type = unassigned DNA
                          organism = Oocystis sp.
```

```
SEQUENCE: 15
atggccgagc cggacgcgaa cggcgcgtcg gatggcaagc gcgcggagat ttacacgtac    60
gagttcccca acctcgttta ctccatgaac tggacggtaa gcaagcacag ttgtagcgca   120
cacagccttg ggtgctgctg cgtccttgct gatggtcatg cttgcgtcgg ccacccgttt   180
tctcacctac cgaaactggc tgcgcacccc tttcagttat gcttgtaatc accgcctcat   240
tacctttgtg tgcagtctcg tcgggacaag aagtttcgac tggcagtggg cagcttcatc   300
gaggactata ataacgtcgt caatatcata tcctgtacgc gccttccccg cactacccag   360
cgtagcggct cagtctgtcg tgcggggttg cacgacagt cgttgggttg aagactattt   420
gaactattgc tgattagtga cgcccatgct ctctcgtaaa gcggggcgga tggctccttt   480
cgcgcccact accatctggc cgcgacctgt ggctctgacg cctcgctggg tctcgacctg   540
ctgaccatac tccctcgtta ctggctgcaa cgcagtggac gaggaacagg gcaagtttgt   600
atgcgacccg tcactgacct tcaagcatcc gtacccaccg accaaggtga tgtttgtgcc   660
agaccgggaa ggcactcggc ccgacctgtt ggccaccacc ggcgactatc tgcgcgtgtg   720
gaagatcggg gaggatggcg tcacgctgca gaagctgctg aacgatgtaa ggctagatt   780
aacgtccagc gctgtgggga aggaccgacg gcacgggccg gaaagggaca tgcatgccgt   840
accggggtg atcacgggcg acggcccacc ggatcatcat cttcctcgct tccaccaacc   900
ctgcgcaacg tccttcgcaa cgtcttgaac aatattttgc atctttcacg ttcatccatc   960
ctcgtcatgg cgaaattaac ttgcagaaca agaacagcga gttttgcgcg ccgctcacat  1020
cgttcgactg gaacgagacc gaccccaagc gcctgggcac cagctctatc gataccacgt  1080
gcacgatctg ggacatcgag aagggcgtgg tggacacgca gctcatcgcg cacgacaagg  1140
aggtgtatga catcgcgtgg ggcggcgtcg gcgtcttcgc gtcggtgtcc gccgacggct  1200
cggtgcgagt cttcgacttg cgagacaagg agcatagcac gatcatctac gagacgccgt  1260
cgccagagac gccgctgctg cgcctggggt ggaacaaaca ggaccccagg tacatgcgca  1320
cgatcgtgat ggactctaac cgcgtggttg tgctggacat ccgcgtgccc accgtgcctg  1380
tcgccgagct gcagcggcac caggcgtgcg caaacgcgct tgcctgggcg ccgcacagca  1440
gctgccacat ctgcacagcg ggcgacgacg cacaggcgct gatctgggac ctcagcgcgg  1500
tatccaagga gggcgactcg ggcctggacc ccatcctcgc gtacaatgca ggtcaagagg  1560
taaaccagct gcagtggtct tcgacgcagc ccgattgggt ggcagtctgc tttggcaaca  1620
aggcgcagat cctgcgagtg tga                                          1643

SEQ ID NO: 16        moltype = DNA  length = 1023
FEATURE              Location/Qualifiers
misc_feature         1..1023
                     note = WD40 repeat protein, cds of 3EUKG2027500, encodes
                       SEQ ID NO: 1
source               1..1023
                     mol_type = unassigned DNA
                     organism = Oocystis sp.
SEQUENCE: 16
atggccgagc cggacgcgaa cggcgcgtcg gatggcaagc gcgcggagat ttacacgtac    60
gagttcccca acctcgttta ctccatgaac tggacgtctc gtcgggacaa gaagtttcga   120
ctggcagtgg gcagcttcat cgaggactat aataacgtcg tcaatatcat atccttggac   180
gaggaacagg gcaagtttgt atgcgacccg tcactgacct tcaagcatcc gtacccaccg   240
accaaggtga tgtttgtgcc agaccgggaa ggcactcggc ccgacctgtt ggccaccacc   300
ggcgactatc tgcgcgtgtg gaagatcggg gaggatggcg tcacgctgca gaagctgctg   360
aacgataaca gaacagcga gttttgcgcg ccgctcacat cgttcgactg gaacgagacc   420
gaccccaagc gcctgggcac cagctctatc gataccacgt ggacatcgag   480
aagggcgtgg tggacacgca gctcatcgcg cacgacaagg aggtgtatga catcgcgtgg   540
ggcggcgtcg gcgtcttcgc gtcggtgtcc gccgacggct cggtgcgagt cttcgacttg   600
cgagacaagg agcatagcac gatcatctac gagacgccgt cgccagagac gccgctgctg   660
cgcctggggt ggaacaaaca ggaccccagg tacatgcgca cgatcgtgat ggactctaac   720
cgcgtggttg tgctggacat ccgcgtgccc accgtgcctg tcgccgagct gcagcggcac   780
caggcgtgcg caaacgcgct tgcctgggcg ccgcacagca gctgccacat ctgcacagcg   840
ggcgacgacg cacaggcgct gatctgggac ctcagcgcgg tatccaagga gggcgactcg   900
ggcctggacc ccatcctcgc gtacaatgca ggtcaagagg taaaccagct gcagtggtct   960
tcgacgcagc ccgattgggt ggcagtctgc tttggcaaca aggcgcagat cctgcgagtg  1020
tga                                                                1023

SEQ ID NO: 17        moltype = DNA  length = 4908
FEATURE              Location/Qualifiers
misc_feature         1..4908
                     note = WD40 repeat protein
source               1..4908
                     mol_type = unassigned DNA
                     organism = Chlamydomonas reinhardtii
SEQUENCE: 17
atgagcgcga gcgacaagcg cgagcggcag gaggtttata catatgtggc accggacccg    60
gtgtacgcca tgaactggag cgtgagttgc cctcgggcac ggctatgacg ggcgctcgct   120
gggctgctgg ggacggggct tgggaagcg gaggcccgtg ccgtctgc agaccctgcc   180
gcttttgtttg ggtggatagg actgtgtcgc ggcaaacgtc cttgcggact gcactggctt   240
gaatgccatg agccaagggg cgctgtggag aggcagagca gagggcgggg atgccaagca   300
gcgcgtggcg tggcggccgc cgcccctgcc tacacctgac tgccctcggg gctgccgacg   360
attgctgact cgctgtacga caaattggcg tgccagaggg ccggggctgt gggatggcga   420
tggcagtaac attctgcaag catgcctctg ctgtgccaac acccaccaca   480
tcgcctgcac ccgctaactt gcccatgacc cacacctaca cccgcacaa cccctgcacac   540
ccgcacccgc aaccataccat accacaggta cggcgggaca agcgcttccg actgggcgtt   600
gcttcattcc gggaggacgt caccaactat gttgacattg tgtcgcgtga gtccaggcgc   660
acacggggcg attgagtaac atggggattg cggacggcag ttacactgtt acggggtat   720
gaagtggagc tgtagagtac agccggagat aagcacatcg ttcggcacag agggagtgtg   780
```

```
tcttggcctt gcccacccca cactgctcca cttccccgcc tccccgcctc cccgctcccc  840
gcctcccccc cgcccccgc ctgcccagt ggacgacgag tcggacgagc tgcgggcgga  900
ccccgggctg cgcttcccgc acgactaccc ggccaccaag ctcatgtgga tgccggaccg  960
cgagggctgt cggcccgacc tgttggcgac cacaggtgcg gcggggctgt ggcggtggtg  1020
gtggtggtgg tggcggcggt cgtggtggtg gtggtggcgg cggtcaggga tgggatgtgg  1080
gttggggggat tgttcgagat gtctggcgca ggtacaagtg gccgggctgg cagcagtgct  1140
gcacttggta acactgccgt tatgtgtctg acacaagccg cacacacgtc tgggctggta  1200
catgcacctg cttcggccgg tttacacgga ttacccgcca acacacacac acacacacac  1260
acacacacac gcacacacac acgtgcacac acaaccacac cacaggggag gcgctacgca  1320
tctggcgtgt gtgtgacggc tcggagggcg aggagagcgg cagcgggccg ggcggacgcg  1380
gcgttcagct gcggtcactg cttaacaacg tgagcggcgt gcggggcgcg cgtttgcgct  1440
gtgtacgctg tcatgttagt gttagggggc acatggaag gcaaacgggc agggcagtgt  1500
gtgcgctgcg tgatctgtgt tgcggtggtg tgtgcgggcc gtgtgccgtc atgggggctg  1560
cgtgtcgcgt gcctgcatag gttgtgggt tgtgtgtatg tgtgtgtggg cgatcacaat  1620
gtggggttcg gacccgggtg tgaggaggg tgggcgggtt gcgcgaactc atcagacgg  1680
cagctgcgct cacgctgcaa gcccatccaa atctacggtc acaactgttt gcacacccac  1740
gaaccccttca aacaaaccgc ccaaacccgc atcaacgttc tcgcacctcg cagaacaagc  1800
agtcggagtt ctcggcgcca ctcacgtcct tcgactggaa cgaggccgac cccaagcgcc  1860
tgggcacctc ctccatcgac accacctgca ccatctggga catcgagtgc cggcgcggat  1920
ggcggcgtgc ggcgtgtggc gtgtggcgtg ggatggaggc tggtggtggt ggcggcgttt  1980
cgtccgccct tgcttaacgt ctcacctccc tggagtgacc tgcagtcgct caccgcggct  2040
gtgtcgctcc tctgtgcctt acgcctccac cgcccccccc catcgcccag caagccatgc  2100
cagtacccc cccccttagct agtcatgaag gtaaacctcc cccgccccac ccctcgtctt  2160
cggagccctg ccaagctcct ccccccacct ctcccccgcc ggcacctgct gtctacttcg  2220
ctacactttct ctgtaccaat ccttgcaacc cccgccggca acgacgcggt tgctgtgcca  2280
ctgtcgcctgg ctacaacttc actttcttggt ttattatgaa tgtagtaacc catctccccca  2340
ccaccccctc ctctcccccca cctgcagaaa ggcgaggtgg acacgcagcc catcgcgcac  2400
gaccggggag tgtacgacat agcctggggt gggctgggcg tgttcgccac cgtcagcgcg  2460
gacggcagcg tgcgcgtgtt cgacctgcgg tgagcggagg ggggcgaga gggcgggagg  2520
gagggaggga gggcatcggg atgggggcgc gggcgggcag gaggccttt catgttatga  2580
tcacagtttt ggagcgctgg cggggatgg cgaggtggtt cacctaaaag caaccatgac  2640
acacgaagat gtaggcagg cgtgggtgcg cgcggggagg gggctgaaag gcgtgcgcct  2700
gcgtggtacg gggttcgtgt ctacggcgca tgggggggtcg tggctgctgc caggcctgtc  2760
gggcgggtgg cacgtggcac gtggcgggtg gactgctggt caaactccga cattcccagt  2820
cccagcccat gtccgcacg gtcccgagcc actcccatcc cgcccttcct cccgccccgc  2880
atccccccatc tcctcctccc cctgccgca gcgacaagga gcactcgacc atcatctacg  2940
agagcccgca gcccgacacg ccgctgctgc gcctgggctg gaaccggcag gaccccgct  3000
acatggccac catactgcag gtgtgcgcg gctgggtata tgtatgtgtg tgtgtgtgta  3060
tatgtgtgtg tgtgtgtagc agctggtggc atttgcgctt ggcagccatt ggccgttggc  3120
aagacaggca ggaacaattc acgatttgga gagcgggacc gttgatgtga tcaggtggcg  3180
gtttgaagcg aacatcaggg tgtgtggggtg gggggggga tcagcaacag ggctaacgcg  3240
gcgggcgcct cagtgcggca ctgacagctg cacgcggtgg cggcaggcga gcgcaaacgt  3300
ggagcgcaag cgtttgctgc gtcgccagtc gcgcgagtgc attgctgtca ctggcggcat  3360
ggtggtggtg atggcggtat gtgtcatgct ggctcagccc ctttccctct ctccctctcc  3420
accacatccg cccttttgcgc tctgtctttc gtggcccatc catctcctcg cctcgcctgc  3480
aggactcgcc caaggtggtc atcctggaca tccgctaccc cacccctgccc gtggcggagc  3540
tgtgcaggca ccaggtgcga ggcggcggag cggttgtgtg caggggcggcg gcggtgggtg  3600
ggtgggttgg ttggttttcta gctgccaggg ttacggcagg ggaaggagca aagacagagc  3660
gatggcagtg cgggcgattg tcgattggag ccagtcgcgg ggtctcggag ggggcccagc  3720
acttgcagtt gaaaggcgct gggttttgcg aggtgaaacg gattgtgttg tgttattgga  3780
gttgcgggac cttctcattg ctgtgctctg tgccgctgtt tcctcacagg cgccggtcaa  3840
cgccttggcc tgggcaccgc actcggccca acacatctgc accgccgggg acgactcaca  3900
ggtgtgcaca aggggtggcg gaatgggca ggcagcgtgt gtggttgtgt gcggtggttg  3960
ggggttgcaa ggattggtac agagaagtgt agcgaagtag acaacaggcg tggggtggat  4020
ttccagcgtg gcttgtactc gagctcctct ccgttggtgt gaccgccaag ccaagccgg  4080
ctgcttccga agctgttttc gtcagcccca tcaccggccc ccggccacct ctgcaaagcc  4140
cgcgcctcgc gctcgcccca acgcaaccct tgcctcgcac cccgtctgcc cacccacgca  4200
caggcgctga tctgggatgt gtcggcggtg gcggcggca acaatgccaa cgcggcggcg  4260
ggcggcggcg ccagtgacgt cagcttggac cccatactgg cgtacggagc ggccagcgag  4320
gtaaggggga tttctgggga tcgggtcttt gggggctggg tttctggtgtt tgcgtgtgg  4380
ggggggggggt gtatgtgtgt gaaagaagaa aacgaaacga tgtgtgtgtg tgtgtgtgtg  4440
tgtcagagag caaggaaaca caggagagag tgtgtgtgca tgtgtgtgtg ttagaaataa  4500
cacgagatag gtgtgtgtat gtgtgtttgc aagcatgcac caaacccagc cgcgaaccca  4560
tcctgtcggt gaggtgcgaa ggggtgcgaag cgtgggttac agccggtgtag tttgcttcag  4620
ctggttgagt gcattggaaa ggcgtgcgcg tcagaagggc tcgcgcgacg agaagagggg  4680
tgtgttccgt gggcatgggg ggctgctggg gtggtggcga agaggaggg cggcgccgaa  4740
gggcctgcgg tttgggctgg gttcgttgcc ggtgctgctc cggccttgtt gcgccccaac  4800
cggcatcccc catcacaatt gcaggtgaac cagctgcagt ggagctccgc gcagccggac  4860
tgggtggcaa tctgcttcgg caacaaaacg cagatcctaa gggtgtga  4908

SEQ ID NO: 18       moltype = DNA   length = 5770
FEATURE             Location/Qualifiers
misc_feature        1..5770
                    note = WD40 repeat protein
source              1..5770
                    mol_type = unassigned DNA
                    organism = Coccomyxa sp.
                    note = Coccomyxa subellipsoidea
SEQUENCE: 18
```

```
gcttgagcgc acaccagata agtgccaagt tcaccatcgc acgtagcaat ttggcagctg    60
ccaactgttg aacacccatt ggtgatcaag gttaggaaaa accacgaact ctgcaggagg   120
atcaaggatc aaatcttgaa gtgatgatag ttggatctca atggtagaat ggatgggaga   180
ctgaatgaca gacgggcgga gatatacacc tacgactctg agaacatcgt atatggcttg   240
agctggagtg taaggatcca ttcagtctat cttcctgaat ttaattgcag cattatgtat   300
tgttccactt gcccctgggt caagtcagtc catgcactct tacttgctac ccctctggag   360
acacagactg actggattgt tctccttgct gggctgcaga accgccgtga caagaagttt   420
cgcctggcag tgggcagctt catcgaggag tacgacaact acgtcgaaat catcacacgt   480
gcgtgccgtc ctagtctcac cttttgcacc ttcacctgca ccgaacctgc cctcccctgg   540
ttgtgaaact ctcctcaaac cacagttgag ccacatgcaa gaaacagagg aagatccgac   600
accaccggct gtttattgct caacttgatg ataattacga gatgaatttg catgagggta   660
ggactggggt gagaggggta gagcactcct tggatggccc aaagccatac cacttacaga   720
ccctcttcca ccaatgtgtt gcagacaggc ttagtgcgca aggagccaga aactgagatc   780
agatgatacc accaaactgt tgaagacagg gctttggtgt cgaaggtcca aagcagaggg   840
gaaaagatag attcggtgct gcagaaaggc ttgcataagc taagattcag acactctcac   900
caatctgttg cagacagtct atggacgcaa gggtgcaaaa attgagatcc atatattctt   960
taccagtctg ttgcagacag gctttggctg cagaggccca aagccgagga agaaagtttg  1020
gttcgggtgt gtagacaggc ttgcagaacc agaggtccac gtactctgac cagtctgtta  1080
cagacagatt cttgggggtgc agaggcataa agcagacggg gaaagattga ctgggttgtc  1140
caaacaggct ttgtgcaggc aggctctatg cagacaggcc tttaagtgca gcttgagaag  1200
cagagaccca gacactctca ccaagctgct gcagacaggc atgggatgca agggtccaga  1260
gcagagctga gagggagaaa gcggttcggt tttacatgac gcctgcagac agtccgagac  1320
aggcttgcag aataatacga ttatctgttc gatagcacaa cgtgcaaatt catcacagat  1380
aagctctggg tgcaaagctt cagaagttga attccagatg ctctcaccca tgacaggcgt  1440
gggtgacaaa gctccagaag ctgagaggga agagtggtt cggttgtaca ggacgcctgc  1500
agccagtctt gagacaggct ggcagagct gacagggaga cattgttttgt ctgcgcaatc  1560
gatgacatga catgcgagtt cacatccgac gctcagatct agacaccctc accaatgcgt  1620
tgcagacagg gctctggatg caacgctgca gaagctgagg agggctggca ttgtctggcc  1680
catcagggct tttttgccgt cgtcaattcg ccgttagggg gagtttatga ttgcagcgag  1740
gtgtagattt tagggttcga tttttagggtt taaggtttaa aaccttattc ccccgtgacg  1800
gcgacgacga tgaaaaaagc catatgcctg ggctgagcag acgggcttgg gttgccaaac  1860
ttaaaaattc gagaatgaac caggggtgtg tggtgcgcgc agtcgatgac gcgacatgca  1920
agttcacgtc ggacgcgcag ctggcgttcc agcaccgta cccacccaca agatcatgt  1980
tcatgccgga caaggagggg gcgcagccgg acctgctggc aaccactgc gactacctgc  2040
gcatctggca gctgaaggag gacggccagc agctggtcaa gcttctcaac aatgtcgcgc  2100
tccttcccta gtaaaattgt ctgtttatta gtatcccacg ctgttgatat ccccccgggga  2160
gattgcgcag cctcaaacaa gcttcaggta aaggtcgaca gctgaaggag gacggcactc  2220
agctgatcaa gctgctgaac aatgtgcgcc cgctctcaga aagacaaatg gagaaagaag  2280
tatgcagaca tcaggcagcg cgagcgctag aagatagaaa aaagggctgg ctcacaagtg  2340
cacgtcatgc aacaacaata caatgatacc cagcccgtac aattcttgtt attgtgaaca  2400
catgctgtca gattacccc ctcctaccaa ggggggggaag gtgcggctgc aaacaagctt  2460
caggtgacag atggctgctg aaggaggatg gcacgcagct ggtcaatctg ctcatggatt  2520
tgcgcctgct ccagcatagt gaccaattat tgtaatctca acatgttgtg tgcaattgtg  2580
tattttctcc ttcgcgccga cagggcccgc cactgtaggc aggatacggc ttacagacgc  2640
ggtaggaacc tactagagat tgtggtggc tgcagcttac ggtgcctgcc atgtagatga  2700
cggaacccat ggtgtggtgg tggtaatggg tttgggccac atgctgtgat gtgctgccct  2760
tctgtatcag agcagtgcat ctcacttcct ggttcaggct gacggattgg aaataactga  2820
gctcaacatc ggaactaagt cttttcaatcc agaaggccct tttcgtcgat cttcgcacgg  2880
aagtggaagt gcaccgccc caatatctgg ttcaagctgg actctttcag gcaggactgg  2940
caggactgag gcttgcttgc gtagttgagc ttgtgcagcc gccacccctg tgcgctggaa  3000
gttagcagtg ctgaattgtg tgtggcttat gtgtgaacta tctgcgcaga acaagaacag  3060
cgagttctgc gcaccgctca ccctccttcga ctggaacgag accgacctga atcggctggg  3120
gacgtcgagc atcgacacca cgtgcaccat ctgggacatc gaggtgactc gctcacaccc  3180
ttgcaccatg atttcaaggg tcttgaacta cagtaagaca catattttct ggcttgcgta  3240
gggccagag cacagtgtcc cctgagctga gaatccctg tgtgactagc ttttacatgga  3300
agcctaacca gatcgcctca tgcagtccta gtcacacagg ggactctttg ttgtatgatc  3360
ttattgaaag atctttttcta gtctcaaagg ggactcttta cctaacgtca aatcagcgcg  3420
ctctgagtgg catatcagat aagggagtgt gtctcaatgt atgtcaccaa ctggacccta  3480
aggccagtct gacctctagg tggttcctca catgatagac cggtactgga catgtcactg  3540
agctgagctg gcgtcgcgt gattgtctct gcagaaaggc gtggtggaca cacagctcat  3600
agcgcatgac aaaagaggtct atgacatcgc ttggggcggc gtgggagtct ttgcgtcagt  3660
ctcggctgac ggctctgtgc gcgtatttga cctccggtgc gcccctgaac tggcaggtgt  3720
cgattgatga gctggcgctg gctcattggg cgatattgga agtgtcttag ggagttcatt  3780
tccttgcata gcagtcagga gagtacttgc atggacaatg aactcgatcg acaaaggcag  3840
ccctcccatg ttcgcccac accctactcc cacacctgga gcaagaggtg aagtgggact  3900
tgtgagggca gaagcacatt gtactggtgt ttacagaaga ctacctctta cgggcctgag  3960
tgccagctgc tgggtctcac aaaagcgccg aaaaaattgc actcctttcc cttgctgcca  4020
aggtctttct tggcgactgc tagagtgacg aagaagtctg taagcaggtt tgaagctcct  4080
tggcactgtg attgtgatca gcgggggggct tgtttgctca tcagcaagga gtgcattgct  4140
gcctgcagat atcatgcagg ctatgcatcc ccgccctcct atctggtgcc ttcatatttg  4200
caggtctacc tcaaactttg gggtacagtg catcacattg aggtgccgct tttgcaggga  4260
caaggagcac agcacgataa tctacgcacag cccgcagccg acacgccgc tgctgaggct  4320
ggggtggaac aagcaggacc cccgctacat ggccacagtc ctcatggact ccaccaaagt  4380
ggtcatcctg gacatcaggt gacacactgt gcttacgctt cttgaataa ttgcactgta  4440
acgggcggcc ctcttctctg cagtttctga atttctgaat ccattacctc tctttaaacg  4500
ctgaatggag tgtactacgc tgggtttgcc cattatgtca acattaacaa tgaacactgt  4560
aattaggaat aataatatgg ctgccagcaa ggtggagggc ttgccaggca tcttcaggca  4620
ccgccctgtg cgcctcggaa aatagaattt caaacttgaa tttggcactt gtgccgcggc  4680
aggtaaccgt ctaggtccac accctcctgg gatgtcagac cctgcttgag cctcggggac  4740
```

```
tctatttcca cctttgtact tttcacccag agggcccaga tgagctgtaa gtggggcgac  4800
ccgtcgcatg agcttgaatt caaaagctgt gccgtggcag gtatccgacc ctgccggtgg  4860
cggagttgca gaggcaccag gcgccggtga acgcggtggc gtgggccccc cactcctcgt  4920
gccacatctg cagcgcgggg gacgatgctc aggcgctgat ctgggatctc tcttccatgt  4980
ctcgccccat ggaccagacc ctgggtgagc ccaccttgat ctagatcatg tgtatctcat  5040
ttgctacacg cctgtcctgc caaaagtcaa gattaattct tgcagacaag ctgcagtaaa  5100
aggctgccac aacctacccc tcgttggcct cgccaaatgc aagcaagacc caatcaaccg  5160
taggcacggt gctcgagctc agtgtttaca ccgcccctg tcagactggg cgtccatgtg  5220
gcaggaatgc tgcaaggagg gagctcgtcg ggttgatggt gtgtgggaag gagtgggcgg  5280
aagattgttg tgcttgaggg gcatacatgt tgtcaaggca tgatgtgctg tgctgcgcag  5340
atcccatcct ggcatacagc gctggggcgg aggtgaatca gctgcaatgg tccacgacgc  5400
agcctgactg ggtggccatc tgctttgcaa acaagaccca gatcttgagg gtgtgagggg  5460
attgcgaacc tgtgaggcgt ttgtctcagt ccaattaaat ctgtgaaggg gtgccagaat  5520
ggatgtacag gagcgtcgag tagaattcta tattcttggt atcgggttac gttcgggttg  5580
ttcctgttgg aacggttgag ctgtgtttta gttctgcctg tctggcacaa aaaaatgtct  5640
gttctggtcc ccgtggactg tgaatgagag aaccggctga gatctttgag aacctattga  5700
catgaaggtt gcagcacatt aagaaaagga ggagcgctct tggtaacctt gctgtaacgt  5760
tgctagatgc                                                         5770
```

```
SEQ ID NO: 19            moltype = DNA   length = 5079
FEATURE                  Location/Qualifiers
misc_feature             1..5079
                         note = WD40 repeat protein
source                   1..5079
                         mol_type = unassigned DNA
                         organism = Volvox sp.
                         note = Volvox carteri
SEQUENCE: 19
atgagcaaca gcgacaagcg tgcggagatt tatacctatg tggcccagga ccccgtctat  60
gcgatgaact ggagcgtaag tgtcggactt tggtgttttt tctccctctt cgcaactcga  120
gccactcata gtcactcgca cttaaggggtc gtaacgtatc gcctgacggg atggtactgg  180
ggtcatgggg ctgacaacca ccgctagctc acttgcatt cccggctgt ggggagggt  240
ggtgtgaggg cggggaggac ggcacaacg gtggcagtgc gtagccctg tccatgccat  300
agtttaaatg ctgcttggag cttgcgttga gctctcgaca cccccatgcc gccgcctag  360
atgtaaggga gcagtaggga cgtcggtgag cgggccccctc ttaaccccct ttccacaacg  420
aaatacacac gcacaccgtg tcggcccggc ccagtcactc cagcccccat ggcttttctc  480
tccccgccga caggtccgcc gtgaccgcg ctttcggttg gcggttggtt cgttccgcga  540
agatgtaacc aactacgtgg aaatcatcag ccgtgagtac ggcagctacg tcggtgatgg  600
ggtccgtct ctagggtgcc acataaggtt gccccttttg ctaagtgtcg ttgttgatac  660
tgttgttgtt gtggtggtgg taatggtaat ggtaatggta atggtaatgg taatggtgat  720
gatgatggtg ggcgtgggtg tgctttgggt gttgcgcatg ggaagtgcgg cttccctccg  780
cccactctcc aacccactct cccccttccc tccccccccaa cacacacact cacacacacg  840
cagtgatga cgatgctgct gagctgcgct ccgacccctc cctgcgcttc caccacgact  900
accccgccac caagctcatg tggcttcccg acagagaggg ctgcagaccc gacctgctag  960
cgaccacggg ggaggcgctt cggatctgga gagttctgga tccggattca gttgcggggg  1020
acggggagga cgtggcggcg gcgggggcag ggggaggagg agcgacgggt gttgggcggg  1080
gtgtgcagct acgagctctg ctgaataacg tgagtttgat ttttggggagg ggggccgccg  1140
tgcgtttggc tgcgtttggg gcgggggacc cctgagatag gttcgtatca ttagctaata  1200
tacttaatat cttgaatatt cctggatttt gcttttacgc tagcagaact tgctattgca  1260
cgtacaccat tattatccat taccgaacca ggaaattacc ataccgccaa gcaactggtc  1320
acagcccttc tgccccaccc ccgggtgccc ccgggtcccg ctcctgctcc cccctttcccc  1380
cccgcccacg gctcattgaa accgccacc cttcagcggc aactgatatc cgatattcct  1440
cagagcttat cactgcagat gaaccttcaa tttactttt attcctatcg acacgggcgc  1500
agacttgttg ccctatcccc tgtggtaggg cccgttcttt gactttggca tcatcacgta  1560
actgaggtgg cccccaggtga ccgacttgac taacattgat gtgcccttc ctgtgctggt  1620
gctggtgctg tgttggtgt tggtgttggt gttgttcaga acaagcagtc cgagttctcc  1680
gctccgctga cctccttcga ctggaacgaa gcggacccca agcggctggg aacctcctcc  1740
atcgatacca cctgcacgat ctgggacatc gaggtgtgtg gagcgtgagg gtggggggc  1800
cctctggggg gctgtggggg ttgggggag ggaaggtgg gagggaaac ccgctgatcc  1860
cgggggtttgg gaccgttgga tttgcgcggg acatgggtat aggggtttcg ggggatcggg  1920
gtttgagctg ggagctgtg gcgtgttggg agagagaagg gagggaaggg tgtgctgagc  1980
ggtgggtttc gtgggctga tgtgtttttt tatgtgagat gtgtgccggt gttgtgggct  2040
tatgttttcct ccctttttcga ccctctgcac ccctctggcc ttcttcctta cacatcacct  2100
agatcccgtt cccctcctc tctcttcgcc catacacaca accacattga  2160
tcgcgtaaag aaaggggagg tggacacgca gctgattgca catgaccggg aggtgtacga  2220
catcgcctgg ggaggactgg gggtatttgc aaccgtgtcg gcacgaggct ccgtgcgcgt  2280
gttcgatttg cggtgggttt ggattgggtt tggattggct ttgtatgtat gtatgtatgt  2340
atgtatgtat gtatgtatgt gtatgtatgt atgtatgtgt atgtatgtgt ctatgtatgt  2400
atgtatgtat gtatgtatgt gtcatgtgt atgtgtctat atgtgtctatgt  2460
gtctatgtga ggtttgggca gtgtggtgag aggcgccatg gcgccgtgg gtttcaggac  2520
acggtgtctc cctgggaccg gacctctccc cgttgactgg ccgggactcg ttaccatca  2580
gcctgatgtg gcgcggccct cgcctcccgc cctacttcaa attcaaattt cccgccctcc  2640
gctgtccggc tcctaccccc ttattgaacg tttcgacagt tgattttcct gagctggctc  2700
ctccttgtat cattagattt cgcttcaccc tttcgctctg ttccgctcta ggcccccgact  2760
ttgctgccc tcctcccgc tcccctagtga caaggagcac agcaccatca tctacgaaag  2820
cccccagccc gacacgccgc tgctgagact gggctggaac cggcaggacc ccaggtacat  2880
ggccaccata ctcatggact cacccaaggt gaggggaagg gagaggggga gggggcccta  2940
agggggagca tggagggcat gcaacgagca aaacttactg gaaattagca tcccccagtgc  3000
ggcagcaaag ccggggagag aggccggagg aaagcctgca gcagcagcag cagcgcgcgt  3060
```

```
cccaagtacc aaaacattcc atatattacg tatacgcttt ctgcacctgt atggggtgt    3120
tgtgtagtgt tgtgatttgt gatcgtacgc gcgtatttgg taaccccccc tcctgctgtc    3180
cggcgcaacg ccccatcgtt gctttgctgc ctgacgtgt atattccctc tgtcccgtac     3240
gttcccgggt gccttgcacg taggaattcc ctcccccctc atttcccac cccgtgtgt     3300
gtgtgtcgt gtgaacccct tacccccccac ccccaccccc caggtggtaa ttctggatat   3360
ccggtacccc acgttgccgg tggcggagct gcaccgccac caggcacccg tcaacgcact   3420
ggctgggcg ccccactcag cacaaacacat atgtaccgcg ggggacgact cgcaggttgg   3480
gaggaggggg gcgggacccg tgggtcggtg cagggaagga tggcgccacg gatgggaaca   3540
cggaagggcc gatattattt gctgttgatg ctacatttgc aggtgacata tggcccgagt   3600
tggcgttttg ccggtgtgtg tgtgtgtgtg tgtgcgtgtg tgttatcccc gtatgtgctg   3660
ctgcacgctg tactgtactg ccccgggtgc tcgtcgaggc ggtcgatccc tcggcacgca   3720
tcctcgcggt ttcttgcata tgattccag ttccctccc cgtcccctc cccgtctcgc      3780
tcgcaggcgc tcatctggga cgtctcagct gtgggcagtg cggtggtca gccgggggcg    3840
ttagggggg gaaccgcggg ggatgtgtcc ctggatccca tcctggcgta cggcgcacag    3900
agcgaggtac ggcagagcag agggggatgaa actagaagtg ggtggtcagg aggatggagc  3960
taatgaacag actgtgcgga agggttctgg agttcggaat gaatcagctg gtactgggta   4020
gtagctggtt ccgatgtggg taccaggtgg tggtcggttc ggcaggtggg cgacagcggt   4080
gtcgtggggc gccgtggaac acatccagct atcttccccg gttaatgagg gcttgggtcg   4140
cattttcttt ggcggggttt catccacagt gattggattc tttggaggag tgcaggccaa   4200
gtagcgcgct ctgcatgatg tgaatgaaca gtgtggtcag cgcagctct gttgcaccac    4260
ccacagaaag ctgcgtcgag cctcggcgcg aatacacgtg tgggctacca ccattgccct   4320
gcattgcagt ccggggatgt gggacgctca tgcagagaaa aaagctgaac cgccttctc    4380
cccaatcggc cgctgggga cgcatgcagc tgatgatgct gccgtcctgc tgccggcgtt    4440
gtctgtccca ccaacacgat ctgcccccctt ccgtaaccct gtctgtctgt ctgtccgccc   4500
ttctatcctg atgttttggg ctgccttttc cttgcaggtg aaccagctgc agtggagctc   4560
cgcgcagccc gactgggtgg ccatatgctt cgccaacaag acccagatcc tcagagtgtg   4620
accccctgtgg gacctgcggc gacttggcta ggcttggata actcagcggc tgcgactttg   4680
cccatgtttc gcactcccgt agtgcagatg gcacgagtgt gggggcaggc aggatcaaca   4740
gcgtcgcctt gcctcaggcc acatgactcc gccatgtctg ggtgtgtagg tccgcgggcg   4800
ctgcataaaa aaagcaatcg tggcattgaa gagcgcggat gcgtgccgaa aaatcttgcg   4860
ttttgcccga gggctgatgg gtcctgggtc gaggaggagg ggtgcggtta gagaggactt   4920
tcacactgaa tggctttctt tgaggagccc tcgaccctg tatgcaaatt tagcctcccc   4980
gtccacaagg aggcatgctg cggctttttg cggcaagctg tccaaaatgt ggcatgcgta   5040
ttccagagga gttttggatg taagcaggtg gaacctggg                          5079

SEQ ID NO: 20           moltype = DNA   length = 3272
FEATURE                 Location/Qualifiers
misc_feature            1..3272
                        note = WD40 repeat protein
source                  1..3272
                        mol_type = unassigned DNA
                        organism = Chlorella sp.
                        note = Chlorella variabilis
SEQUENCE: 20
gtgaactcgg ccggttgcca tccaggagag agccaacccc tgagcccctg cacgggtgag    60
gaccgtcgga ggaaggcgca gaatgccggc gcggggcgcc agagcggggg agtgcgggcg   120
ccgaccgccg cccagcagca gcagccgcgg ccgcttagca ggcgccctt gtgggggtc     180
gtgcgcttat ctcctcgcat tctctcttac aggctcccat gcaggaccag cagcagcagg   240
gggaggggcg ggcagagatc tacacctaca gcagctcggc cagcgtctac gcctgcggct   300
tctcggtgag cagccagcca atggcagcgg ccgccgtcag ctcttccagc ccagagtgca   360
gcacagcag cgcagcagc gcagcacgaa gtctcagagc atgtcggccg ctgcgctgca   420
gccgtgtgcc cggcagctta ccgccactct cgccgctccc gccgctgcgt gcctcccttg   480
cagtcccgcc ccgacaagcc cttccgcctg gctgtcggca gcttcatcga cgactatgca   540
aacaaagtgg agatcatcca gtgtgagtgt ctgttttttag gcaggcgctg cgctgcacgg   600
actgcggatg gcacggtgct gccgcggctg ctgtgattgc acgcggctgc tgctcgggtc   660
tggcgccgcc gctggggtgg gatcttgtct ggctctggct ctggatcttc atctggggcg   720
cagtcttggg catgtgggtg gtagcacgct gctcagacca ggcccacct gccgccacca   780
ccactgccta tgcgcgccac ccgcagtgga cgaggcggcc ggggtggtgc gcaacaaccc   840
tgcgctgacc ttccagcacc cctacccgcc caccaaggtc gccttcatcc cggataaggt   900
gaggcgccga ggccgggctg actgagccag gttgtgggct gcctgccggg acaaggcagc   960
agcctgcggg tgctgtcctg ccccctgcccc tgacctgacc gtgctgcccc gtatgctggc   1020
tctgtgatcc ccgccttctg aacgccacca cctgccgccg ccgcctcctg ccccagagcc   1080
ggacccgccc cgacctgctg gccactagcg gcgacttcct cgcgcctgtg gcgtgtgtcgg   1140
atgagccgga ggcgcagcag ggcgtgcgcc tggagaatgg gctgaacaat gtgagggcgg   1200
gcgggcgggc ggctgcgctg caggggggtgc tcagcgaggg tgggagcagg ggtaggggcg   1260
cctcggtgcg gcgagtgccg gcagggctgc tgggagcga cgtgccggcc agtgtacaga    1320
gcgcaccctc gccgccagcc ctcgacgcgg cgctcgcacc acctcacacc ctgccgtctc   1380
cctctctccc ccatgctccc atgtcccat gctccccctc ccgcccgcca cccgccgcag    1440
aacaagggcg gcgactttgc ggcgccgctg acgtccttg actggaacga gctgacccct   1500
cgccgcgtgg gcaccgcctc gatcgacacg acgtgcacga tgtgggacgt ggagcgcggg   1560
gtggtggaca cgcagctcat cgcgcacgac aaggaggtgg gtgggtcgg cgcgggggt    1620
gtagtgtggc cacgggcgtg gcgtgcctgc ttgtgggtgg agcatggggt ggtggtcagg   1680
ccgcagttga ttgcgagcta caaggggggtg ggtggggtgg tggcttctct aggcggtgct   1740
ggtcctgtgt tcagcatgc gcttgagcat atgtgcacac cgattgcatg gagggtgtg    1800
ggcggtggtg ggcatcaaca tcacacctgc ctgccctgc ccgccctca aagacctcgc    1860
tgccgcccgc ccgcctgccc gcctccccca cacacatcta tgccaggtgt acgacattgc   1920
ctggggcggg gtcgggatct ttgcctcggt tccgccgac ggctcggtgc gcgtgttga    1980
cctcaggtgg gaacagccgg ctcacccgcc agccgggctg cgtgcccgcc tgcccagccg   2040
cttgccctcc ggcgcagccc gtgcacactt ctgcgagctc cgccgccagg ccgcaaaccc   2100
```

```
acgcacgctc gtggcccgc cagaaaccca cgcacgcacg ctcacccgct tgcgcatgca  2160
tgcacttatt gttgtttgcc cacagggaca aggagcactc caccatcatt tatgagtccc  2220
cccagcccga caccccctg ctgcgcctgt cctggaacaa gcaggacccg cgctacatcg  2280
caggtgcggc gcggccggcg cggggcctcg cggtaccatc gtgccccagc cgagctgcct  2340
tgcggctgct caggccagg cacacaggca ctcaagcaca ccaccacaac caccacagcc  2400
accactttca cacccacgca cacacaagcc gttccttccc tgcgtgcagt gttagccatg  2460
gattcgccgc gggtgacggt actggacatc cggtacccca cgctcccgt ggccgagctg  2520
cagcggcacc aggcggggt caacgccatc tgctgggccc ccacagcgc cacccacctg  2580
tgctccgcgg gcgacgacag ccaggcgctg atctgggacc tgggcctgct gggcacgctg  2640
gggcagcagc ccgagggcgg cccgccgggc gccgcggcgg cgggtggcgg cctggaccg  2700
atcctggcct acaacgcagg cgccgaggtc aaccagctgc agtggagccc cgcccagccg  2760
gactgggtgg caatctgctt cggcaacaag acccagctgc tgcgggtgtg aggcgcgtgc  2820
cgacagagca ccacaccgcc gcgctgctcg ccggctgcag cgttgctcgc cgctcccctc  2880
cagggcagcg cggcgcccgc gccgttcctg cttcccaagc tgccagcctt cttgcgtccc  2940
ttattcgcct gctccccctg tcttgcttcc gctcctgctg tactgccccc cgcccgcatc  3000
tgtatcaccc gggtgccttt tcttcactgc acacgtacca ccgcatcgtg ggcaccctgc  3060
ccctccctaa tgcacggccc tctggcacgc tgccagcccc tctaatgcat gggccctgcc  3120
attcacacca atcgcatcaa ccgtacatct gtcccccgc actgctcttt gtcaccattc  3180
cacctgatgc tctctcctct cccaacccaa ctgatccccc cgtcgcatcc ataccgattt  3240
cgagagacac cttgcaatga aacacgcagc gc                                3272

SEQ ID NO: 21         moltype = DNA   length = 3032
FEATURE               Location/Qualifiers
misc_feature          1..3032
                      note = WD40 repeat protein
source                1..3032
                      mol_type = unassigned DNA
                      organism = unidentified
                      note = Parachlorella sp.
SEQUENCE: 21
atgcagcgcg cagaaatcca tacgtacgag agccccacgt tggtttatgc actcaactgg  60
agtgtaagtc acacaatatg ttgacaagat actgaagcgc gacatgtata ggctgtgtcc  120
tgaagaggca agctttcacc tgctgtaggt gcggcctgac aaaccttca gactagccat  180
cggaagctac atcgaggact acaacaaccg agtgaaatc gtcacacgta tgttcaccgc  240
ttcaggtctt gctgctattg cgttcgtgcc ttcaaagtca gacttttcgaa gcaagtttgc  300
ccaccggggg tctctggtgc agtcggtgaa gatggaaatg gaatgcgcc tagcccacgg  360
cacacctttc agcatcccta tccacccacc aaacttcagt ttgtaccaga tcctgatggc  420
tccggcctg atctgttagc cagctccggt gacttccttc gactctggcg catcacggag  480
gacggggttt ccctggaaaa gcttctcaac aacgtgaccg cgctgctct gatagcgctg  540
tcctggtgta ccatgacgg ctagcgcaca gcgtagcgc gcagtgcaac gaagacgacc  600
ggggctgacg ctactctgaa tgcaaccacc ttgcctgctg tggtgcagaa caaagcaagc  660
gagttttgcg cgcccttgac cagctttgac tggaatgaga cgaccccaa gagggtgggc  720
actgccagca tcgacaccac ctgcactgta tgggacatag agaaggggt ggtggacacc  780
caggtgggtt gagtggagta gagtggagtg gcggagaacc tggaagagca ggccatgacc  840
agggcatgcg tgctgagcac tcctgccgcc gccgcgtcg cgtcaagtct tggccgttca  900
aagactcgag gtccttccgg tgtgctgctt ggagtcgccc gcgtcctgcc acatcgtgtg  960
cctgctgccg ctttggagcc atgctcccct tgccacgcgc tcacccttgg aaccgtgtgg  1020
cccctgcagc tgattgccca tgacaaggag gtgtacgaca tagcatgggg gggcgtgggg  1080
gtgtttgcct cggtgtcagc agatggctcg gtgcgggtgt ttgacttgag gtaggtgctc  1140
tgcctgcggc cttcgacctg gggctgagtg accgggtggg gccggcctgg aggatggagg  1200
gtgaaatatg gtgcagtacg cgaggtacat gatcttgcgg ttggctcatc ctggtgtggg  1260
tcgctggtag aagaagcggc gtggaacagg tgtaggtgtg gggcttggag cagtgaggtg  1320
caagccagtt gtagagtatg cccagcagc ctccccaaag ggccccagc ccgcagcacc  1380
ctgccagcag gagcttcccc agttgctgcg ccaggggcag cgcatgctcg ggcgcacagc  1440
tgtgtgtgtg cacgacagag ccagctcctg tgtgtggagct gggtgggc acgtgtggga  1500
gggctctgtt ggggtcccat gcgttagaca gggcatggca ggggtctggg cgtgtgggca  1560
ggtcgtgctt ctgcctcatg cgccctccac ccaccctcac cccgctgctg cctcatacgc  1620
cccgcaccca ccccctcccc ccttcctgcc gctgcctcat gcgccctcca ccaacattcc  1680
ctgcagggat aaggagcact cgaccatcat ctatgagtcc ccgcagcccg acaccccct  1740
gctgccgctg cctggaaca agcaggaccc gcgtacatg gccaccactg ccctcaactc  1800
ctccgccatt gtggtgctgg acatccgatt ccccacggtg ccggtggtgg agctgtccaa  1860
gcaccaggtg cgatatggca gcggggtgc agtcgctgcg gggggtgcct gcaatggggc  1920
agctgctatc tgccgccttg ctgtgagctg gcctggcgct gggagccagg agtgctcacc  1980
ctgctgcgag cgctgccacg ggttggctgc atcgcacagc ctgaggcccc cgggctggcc  2040
tggaagggcg ggtgcctcac cggctcaggc gcccacgagg atcgccgatt tcctgccctg  2100
gcctggtgat catgccgctg gcggcggtgc ggtggcgtgc gcagcatgcg gctgcgcact  2160
gcattggcca gccacgctgc tcgtgccatg gtgtgcatgc agcccgcacc agccaaagcg  2220
tgctcgcgct gcccgctgct gaacagacct ctcaacgcgc tccctccctc tgtggctagt  2280
gtgccccagc accaggtggc agctggagcg cgcccagcag gttgcagcaa caggaggaaa  2340
gccgccgccc ctgggcctgc gggcaattt agcgcgttgc gctgcgctgc attcctcgca  2400
acgtgcacgt caccgaagcg tgtatctccc ccctttccca ctgcctgcag gccgcctgca  2460
atgctgtggc ctgggccccc caaagtgcca accacatctg cagtgccggg gacgattgcc  2520
aggtgggcg cgctggaagg ggggaaggaa aggggggagg ggtcctgtg aactgggcag  2580
aatgctgcac ttttctaata accgccacca acaagctggg gctgtgcttg gggaggggca  2640
gggcagtcgt cccccgcgc acggggccg acacccttgc cttcccttgg cgagtattcg  2700
agcacgggac cccttcctcc cctcctgtgc atctcatgtg atgtactcgc cgagccctct  2760
gccccctgctg cgactgtcgc gcagctgcaa ggccacgcgc caagcgcatt gcggcgctgt  2820
ccctccgcgc ctctgtgccg tgcgtgcagg ctttgatctg ggacctgtcc actctggggg  2880
agggcggcgc gggccaggcg gggagccccc ccctggaccc catcctgtcc tacatggcgg  2940
```

```
gggcggaggt gaaccagctg cagtggtcgg cgtcccaccc cgactgggtg gccatctgct   3000
ttgggaacaa gacgcagatt ttgagggtgt ga                                 3032

SEQ ID NO: 22            moltype = DNA   length = 1045
FEATURE                  Location/Qualifiers
misc_feature             1..1045
                         note = WD40 repeat protein
source                   1..1045
                         mol_type = unassigned DNA
                         organism = unidentified
                         note = Picochlorum sp.
SEQUENCE: 22
atgtcgactg attggttggt tgtaattgtg cagtctaggc aagataaggg tgtacgagta    60
gctgttggca gttttgtgga gggtgtctcg aacacagtcg agattcttcg cggtacggat   120
catctgtgag tctctgttct acttgggaaa tgtgggcata atttttttgta tatgaggtgc   180
agtgactccc gcaggtttaa ttgtggatga caaggaaacg ttcggcatag agtatccggc   240
gacgcaggtg ggatttattc ctgataggtt ttgcaacaag ccagatttgt tggcaacctc   300
tggggatgct gttaggttgt ggaaaatttc agacgcaggg acgacgcttg aactggtgtt   360
gaatgatcca agaataccct ctaaaaattt cagtgcggtg acctgctttg attggagtga   420
aatcaatgtg aaagtgttgg cggcagggtc gagtgcaggg cgattattgc tgtgggacac   480
cgagtcaggg aggctgcagg gcacaatggt gggacatgag gatgagattc ttgattgtca   540
gtgggcagct aatgatgtga ttgtttcttc ttcggggcgat ggatcaattc ggatgtatga   600
cctgcgggat aaagaccatt gcacggtatt gtatgagacc cccaggagga ccctgtgcc   660
gaggttttgt tggaacaagc tggatccgag gcatcttgca tttttcatag aaaagagtcg   720
gcttgttagt gttctcgatg ttcgctttcc gacagagccg gtgatcttgc tggacggtca   780
tatgggaaac tgtacagcac ttggttggtc ccctcacaga gaggaatacc tctgctcagt   840
tggagatgat tgccatgcat tgatatggga cgtggggaag gtgaatagtg aggaggatag   900
taagccaaat cgagaggcgg tggacgcatc tcctatccta gcgtacaatg ctcaggcaga   960
gatcaatgcg atggcttgga atccaataga cccagattgg attgccattt gcgctagaaa  1020
cagaacacaa gtattgagaa tatga                                        1045

SEQ ID NO: 23            moltype = DNA   length = 2857
FEATURE                  Location/Qualifiers
misc_feature             1..2857
                         note = WD40 repeat protein
source                   1..2857
                         mol_type = unassigned DNA
                         organism = Tetraselmis sp.
SEQUENCE: 23
atgccgacga gcgacgcgac gcaggcacat gagcaccatc acgtgccgca cgcgcggccg    60
cgaccccgc caagaacgtt gtctgcatgt gccatgttga tgagcaagga gaaacggcgg   120
cgccacgcag acaagagctg gccgattttt tggccagtgt gtgtgtggct agctttcgcg   180
agctccacca agaaagcctc agcgtgcggg ccagctcgct ttgcataatg cttcggcaat   240
ttgattgttg actagccgct acagtacatg tacaacggag cgtcgcctac gggtatacgg   300
agggcttgcc gtaactgtgg atcgctgcct attaaacggc cgtcgtaaag atagacgctg   360
caaggggttc actggtgtca gtcctgtccc ggggcggga aaaccaaaac cctggtcgta   420
aatgagacgt ggcaaagttt caccgagcgc agtcgcgtat ccaggaaaaa aaaaccccgt   480
ccctcgcact cttcgtggcc acaggtagag gactgccgaa gtgatcaccc cacagcaaag   540
cccaccgtcg tcagcgctac ccgttacgtg cgggtactca gactctcgcc gcgacaccca   600
cgcaacaagc caacaacgcc gccccgcttg cggatcgctt cacgcttggg ctggtgcgga   660
accttgttca gggaccttgt tccgccgac aaattattgc tgctcggctc tcctgcactc   720
cgacagcgtg gcaccaggct ggcctgttca ccgcccgggg ccggtgtggg ttgtggccca   780
cgcgagtggc cactcgggtt cctttcagcc tacgctgggc gtaaagccct taccagcatg   840
cttgtcctgc acgcgcccg tgctgccacg ggctgacgca ctgatcctgc cgtgttgcgc   900
ttgtggccgg aggctcggtg ctgtgccccg ggcgacgcgc gcctgggtgg gctagcttgc   960
gatgccgagc gggccggagg accggggtgc gggggcggcg ggggcggcgc cccaccaacg  1020
aggcgatagc aacggcaaag cggtgacaga caagcgcggg gagatataca cctacgaggc  1080
gccgtacccg gtatacggga tgaactggag tgtgcgtgcg ccggacatgg ccaagggggg  1140
ccaggggagg ccccccgggg ggggggggg ggggaggagt tacttggtac aagcagactt  1200
tggccccgtg gctgaggggg tcgagtgttg caggtgcgg aggatatgaa gttccgcctc  1260
gcggtgggaa gctttgtaga ggacgtggag aatgcggtgg agctcatccg gcgtgagtgc  1320
ccgagcgcgt acgcaggcct gcctgctgtg tgcagggagc gcgcgggcat ccgcctgatg  1380
acgtgctgtg tgcacagtga acgaggaaac cggcaagttt gagagcaacc cggcgcacaa  1440
gtttgtgcac ccgtatccac ccaccaaaat aatgtttatc cccgaccgcg actcgcg    1500
ccctgacctg ctcgccacca cgggcgatta tctcgggctg tggcgcgtgg aggaggacgg  1560
cgtcacgctg cacaagctgc tgacaaatgt gagcgcggac aaacctttgt gcccgccccc  1620
cccccaccac caccagtcct ccttccctct aaggcccatt ctcaagagat accacggcca  1680
gctccagcat gaccccgcc cccctatttc gtcaacatgc acctcccccc tgcagaacaa  1740
aaacagtgag ttttgcgcgc cattaacatc ctttgactgg aacgaagccg acccgaggca  1800
actgggcacc tcatccatcg acacaacatg cacaatatgg acatcgagg tgggccaggc  1860
agtccaagcc ccccccccc ccccccccc gcaaatgccc tccttgcgct acatgtcaa  1920
aacgcctgcc tcgtggtgcg tccagagagg cgttgttgac acgcagctta tcgctcacga  1980
caaggaggtg tacgacattg cgtggggcgg gcagggcgtc tttgccagcg tgtccgcaga  2040
cggctctgtg cgagtgtttg acctccggtg cgtgtcgcg tacctgcggc actgtcgtg  2100
cccacctggg cgccgtggct ggcttgcggg gggggggggg gggggctga cgcgccggcg  2160
ggctgttcgg caccgcaggg acaaggacca ctcaaccatc atctacgaga gcgggatgcc  2220
cgagatcccg ctgctgcggc tgggctgaa caagcaggac ccgcgctaca tggccaccat  2280
cctcatggac tcctccaagg tggtcgtcct ggacatcagg tccgccgccc ttgcctgcca  2340
tcacgcaaca tatactgggg gtgtgtctgg cggcgctgac ctgtgatgct gcgccgccgt  2400
```

-continued

```
gcctgctgca ggtaccccac gatgcctgta gctgagctgg aggcgcatca caagcctgtg    2460
aatgccctgg cgtgggcccc gcagtcctcc tcgcacatct gcactgcggg ggacgacgca    2520
caggtgtggc gggatgcatg ctctgatgca tcacaggaga cagagcgaca gggggggggt    2580
gagcaggggg ggggggggg  ggaaggggg  atgcccgggt gaggcagatg gtggctgact    2640
gttgcatgct gccgcccagg cgctcatctg gaaccttgcc ccatgggcca cccaggggcc    2700
catgggggt  gctgcgcctg cagttctagg cgcggacctg gatcccatcc tagcgtacaa    2760
cgccggcgag gaaatcaatc agctgcagtg gtccagcacg cagtccgact gggtgggcat    2820
atcctttggc aacaagatcc agattttgag aatctag                             2857

SEQ ID NO: 24           moltype = DNA   length = 1431
FEATURE                 Location/Qualifiers
misc_feature            1..1431
                        note = WD40 repeat protein
source                  1..1431
                        mol_type = unassigned DNA
                        organism = unidentified
                        note = Ostreococcus sp.
SEQUENCE: 24
cggtcgacgc gctcgacgcg gtcgacgcga gcgaggcgcg cgcttcgagc gacgcgaagg     60
cgtcggacgc gaacgcgaag gcgtcgagcg cgaacgcggg accgacgggg cggtgaaggc    120
gcgcgacgaa agacgaggaa ggcgcgcgcg aacgatgaac gcggagaaga gggcggaaat    180
atacacctat gaggcgccgt ggatgatcta cgcgtgcaat tggacgtgc  gtggcgagga    240
aggcgatgga ttgggggcga gcgcgggaga attgaatcgc gaggggcgac ggaggagacg    300
cgacggagga gactcgggga cgcgcgcgaa cggtcgatcg gagattaaaa atggagacgc    360
gcgagtgaag acgcgaatgg cgtggactga cgacgtcgaa ttgaacgcga caggttcgac    420
aagataaacg cttccgcctc gccttgggtt cgttcgtgga ggagtatagc aacaaggttg    480
agatcatcac cttggacgag gaaaccgggg agtttccgga ggaggcgcag tgttcgttca    540
cgcatccgta tccttgcacg aaaatttttgt tcattccgga caaggagtgc acgaaggagg    600
atttgttagc gacgacgggg gactacttgc gaatctggca agtgcaggat gataacacgg    660
tgcagatgaa atcttactg  aataataaca agagcagcga attttgcgca ccgctgacga    720
gctttgattg gaacgagacc aagcttcagc gagtgggac  gtcgtcgatc gacacgacgt    780
gtacgatttg ggacatcgag cgcgagtgcg tggacacgga gctcatcgcg catgataagg    840
aggtgtacga catcgcgtgg ggtggtccag aggttttcgc tagcgtaagt gcggatggaa    900
gtgtgcgagt tttcgacttg agagacaagg atcacagtac gatcatttac gagagtcaaa    960
ctccagacac gccgctgctg cgtttgggt  ggaacaagca ggatccgaga tacatggcca   1020
ccatttgcat ggatagtccg gtgatcattc tcgatattcg cttcccgacg ttgccggtcg   1080
cagaacttca gagtcacaga gcgagcgtga atacattggc gtgggcgcca cacagctcaa   1140
gccacatgtg cacggcgggc gacgacagtc aggcgttgat ttgggatttg tcgtccatga   1200
atcaaccacc cgaaggcggt ctcgacccta ttctcgctta ctctgctgga gcagaaatca   1260
atcagttaca gtggagcgcg tcgcaaccgg attggatctc gatagctttc cgaaacagcc   1320
tccagatcct ccgagtttag tcaacgcgct gtcaggtctg cgccgacgcc actgtatatt   1380
acccgaattt ccggatacgc gacacacgac acacgacacg cacgcacgta g            1431

SEQ ID NO: 25           moltype = DNA   length = 1294
FEATURE                 Location/Qualifiers
misc_feature            1..1294
                        note = WD40 repeat protein
source                  1..1294
                        mol_type = unassigned DNA
                        organism = Micromonas sp.
                        note = Micromonas commoda
SEQUENCE: 25
atggcggcca tgggcagcgg ccagagcggc gccgagattt acacgtacga ggcgccatgg     60
ctcgtgtacg cgatgaattg gagtgtgagt gcccgtcgat gactctgctc cgtcccgccg    120
cgttcctccc cgcccgggcc gatccctcgc ctgcacccaa tctgacccgg caagatccgc    180
tgctgacgcg actttgagga cgcgcccggc agtcgaccga cgcgcccgc  ccgcgacgt     240
gacccgctga cgcttcactc gatataaacc tccccctccc cgcgcgcgca ttcaacaggt    300
gaggcaggac aagaggttcc gcctcgcgct cgggtcgttc gtggaggagt acagcaacaa    360
ggttgagatc atcacgctgg acgagcagcg acgggagttc ccggcggagc cgacgacag    420
gttcgaccac ccgtacccgt gcacgaagat catgttcgtc ccagacgccg agggaaccag    480
cgaggactta ctggccacga gcggcgacta tctgcgggtt tggcgcatag gcgacgacgg    540
cgtgcacctg cggagcctcc tgaacaacaa caagaacagc gacttttgcg cgccgctcac    600
gtcgttcgac tggagcacca ccaacctggc gagggtgggc accagcagtt tggacaccac    660
gtgcaccatc tgggacctgg agaaggagac ggttgactgc cgctcatcg gcacgacaa     720
ggaggtgtac gacatcgcgt ggggcggcc  ggaggttttc gcgagcgtct ccgccgacgg    780
gagcgtcagg gtgttcgacc tgcgggataa ggaccacgac acgatcgtct acgagtcccc    840
gacgccggac acgccgctgc tgaggttggg ttgaacaag  cagaacccga ggtacatggc    900
gacgatggaa atggacagcg ccaaggttgt ggtgctggac attcgcgtgc ccgcgctgcc    960
ggtggccagg ctgaagaagc acagagccgc ggtgacaacg ctggcgttga cgccgcaacg   1020
ctcgaggaac atatgcaccg ccggggacga cgcgcaggcg ctcatttggg acctgtcgtc   1080
ggtggcgcag cccggggagg acgggatgga tccgatgctg gcgtacaacg cggggcggaa   1140
gatcagtcag ctgcagtgga gcgcgacgca aaccgactgg atagccatcg cattcggcaa   1200
aaacctgcag gtgcttcacg tgtgacgccc gcggggagaa cgtggcgatc gtagtcctag   1260
ttcggttttg aattcaacgt tcatttagca ctca                               1294

SEQ ID NO: 26           moltype = DNA   length = 1041
FEATURE                 Location/Qualifiers
misc_feature            1..1041
                        note = WD40 repeat protein
```

```
source              1..1041
                    mol_type = unassigned DNA
                    organism = Arabidopsis sp.
SEQUENCE: 26
atgggaacga gcagcgatcc gattcaagat ggttccgatg agcagcagaa gcgatcagag   60
atctatacat acgaagcgcc atggcacatc tacgcaatga attggagcgt tcgtcgcgat  120
aagaagtatc gtctcgccat cactagcctc ctcgagcaat acccgaaccg tgtcgagatt  180
gtgcagctcg atgaatccaa tggtgagatc cgttccgatc ctaacctctc ctttgagcat  240
ccttatccac caacgaagac cattttcata cctgacaagg aatgccaaag acctgatctt  300
ctcgctactt caagtgattt ccttcgttta tggagaatcg ctgatgatca ttcccgtgtt  360
gagctcaaat cttgtctcaa tagcaataag aacagtgagt tttgtggtcc tcttacttct  420
tttgattgga atgaagctga gccacgtcga attggaacat ctagtactga tacgacttgt  480
actatctggg acattgagcg tgaagctgtt gatactcagc ttattgctca tgataaggaa  540
gtttttgata ttgcttgggg tggtgttggt gtttttgcat ctgtttcagc tgatggctcc  600
gttagggtgt ttgatcttcg tgataaggaa cattcgacga ttatctatga gagctccgag  660
cctgatactc ctttagtgcg tcttggttgg aacaaacagg atcctaggta catggctact  720
attatcatgg acagtgctaa agttgtggtg cttgacattc gttttccggc tcttcctgtg  780
gttgagcttc aacgacatca agctagtgtc aatgccattg cttgggctcc tcatagctct  840
tgtcacattt gtactgctgg agatgattct caagctttga tttgggatat ttcatccatg  900
ggacagcatg ttgaaggtgg tcttgaccct attctagctt acactgctgg tgctgagatt  960
gagcagcttc agtggtcctc ttctcagcct gattgggtcg caattgcttt ctctactaag 1020
ctgcaaattc tcagggtttg a                                           1041
```

METHODS FOR PRODUCING A COMPOSITION CONTAINING LIPIDS FROM RECOMBINANT ALGAE HAVING HIGH LIPID PRODUCTIVITY

CROSS-REFERENCE TO RELATED APPLICATIONS

This application is a continuation application of U.S. application Ser. No. 17/519,383 filed Nov. 4, 2021, now pending; which claims the benefit under 35 USC § 119(e) to U.S. Application Ser. No. 63/110,301 filed Nov. 5, 2020. The disclosure of each of the prior applications is considered part of and is incorporated by reference in the disclosure of this application.

INCORPORATION BY REFERENCE OF SEQUENCE LISTING

The material in the accompanying sequence listing is hereby incorporated by reference into this application. The accompanying sequence listing xml file, named SGI2290-2_ST26.xml, was created on Mar. 29, 2024 and is 73,099 bytes in size.

BACKGROUND OF THE INVENTION

Field of the Invention

The invention involves the provision of a recombinant algal mutant organism and methods for the production of lipids.

Background Information

The production of biofuels presents great opportunities to develop environmentally sound sources of energy that can be obtained at reasonable cost. Efforts have been directed towards using algae or other microorganisms to produce hydrocarbons that can be used as biodiesel or other biofuels due to their high lipid content. Additional specialty chemicals can also be obtained from these organisms and for use in consumer products.

Since algae use energy from sunlight to combine water and carbon dioxide to produce biomass, achieving increased productivity offers the possibility of a carbon neutral fuel source. The development of algal strains with very high lipid productivity for the production of algal-sourced biofuels therefore presents the possibility of a significant reduction in new carbon dioxide released into the atmosphere and a consequent reduction in the problem of global warming.

The development of commercially viable algal biofuels requires strains with high lipid and biomass productivity. Even the most productive wild type strains are not sufficiently productive to permit an economically viable development of this resource. Strategies for increasing algal production of biofuels and other products have included modification of nutrition provided to the organisms, such as cultivating the organisms in nitrogen, phosphorus, or silicon deficient media. Other strategies have included modification of cultivation conditions or environmental protocols, or various efforts directed towards genetic engineering of the organisms. While engineering algae strains to have a combination of increased photosynthetic efficiency (resulting in increased overall biomass productivity) and/or high lipid productivity could provide a solution to this problem, deficiencies still remain. The development of more productive strains continues to be a barrier to efficient utilization of this energy source.

SUMMARY OF THE INVENTION

The invention provides recombinant algal mutants that have a genetic modification to a gene or nucleic acid sequence encoding a WD40 repeat containing protein. The genetic modification of one or more nucleic acid sequences encoding a WD40 repeat containing protein results in a mutant organism with increased lipid productivity and/or higher biomass productivity (as measured by total organic carbon). In some embodiments the genetic modification is a gene attenuation, or a deletion, disruption, or inactivation. The lipid products of these mutants can be utilized as biofuels or for other specialty chemical products. Methods of making and using the recombinant algal mutants and methods of producing lipids are also disclosed.

In a first aspect the invention provides a recombinant algal organism having a genetic modification in a gene or nucleic acid sequence encoding a WD40 repeat containing protein. The recombinant alga exhibits higher lipid productivity and/or higher biomass productivity versus a corresponding control algal cell not having the genetic modification. In one embodiment the recombinant alga is a Chlorophyte alga, which optionally can be of the Class Trebouxiophyceae. The gene or nucleic acid sequence encoding the WD40 repeat containing protein can have a nucleic acid sequence having at least 75% sequence identity to a nucleic acid sequence of any one of SEQ ID NOs: 14-26. In one embodiment the gene encoding the WD40 repeat containing protein has a nucleic acid sequence having at least 75% sequence identity to a nucleic acid sequence of SEQ ID NO: 15 or 16.

In one embodiment the genetic modification to the gene encoding the WD40 repeat containing protein is a functional deletion. The genetic modification of the gene encoding the WD40 repeat containing protein can result in an attenuation in the expression of the nucleic acid sequence. In one embodiment the genetic modification of the gene encoding the WD40 repeat containing protein is a deletion of one or more amino acids in a polypeptide sequence of a WD40 repeat containing protein. In one embodiment the genetic modification of the gene encoding the WD repeat containing protein is a frame shift mutation. The genetic modification can also be a deletion, a disruption, or an inactivation.

In one embodiment the recombinant alga has at least 30% higher lipid productivity versus a corresponding control alga that does not comprise the genetic modification. The recombinant alga can have at least 15% higher biomass productivity as measured by total organic carbon versus a control alga that does not comprise the genetic modification. The recombinant alga can exhibit at least 40 grams per square meter per day of lipid production after 5 days of cultivation.

In various embodiments the recombinant alga can higher biomass productivity per unit time as measured by production of total organic carbon (TOC). The recombinant alga can have higher biomass productivity under nitrogen deficient conditions. The recombinant alga can have higher total organic carbon production under nitrogen deficient conditions. In some embodiments the recombinant alga is of a family selected from Oocystaceae, Chlorellaceae, and Eustigmatophyceae; and the recombinant alga can be of a genus selected from *Chlorella*, *Parachlorella*, *Picochlorum*, *Tetraselmis*, and *Oocystis*.

In another aspect the invention provides a lipid containing product produced by any of the recombinant algae described herein.

In another aspect the invention provides a biomass product containing any of the recombinant algae described herein.

In another aspect the invention provides a method of producing a composition containing lipids. The methods involve cultivating a recombinant alga described herein and thereby producing a composition containing lipids. The method can also involve harvesting a lipidic composition from the recombinant alga. The method can involve producing a genetic modifications to a nucleic acid sequence encoding a WD repeat protein, which can be a functional deletion. The functional deletion can be obtained by subjecting the algal organism to ultra-violet light. In some embodiments the gene encoding the WD repeat containing protein has a nucleic acid sequence having at least 90% sequence identity to SEQ ID NO: 16. The algal organism can be a Chlorophyte alga, optionally of the genus Oocystis, but can be any recombinant alga described herein. The recombinant alga produced by the method can have at least 30% greater lipid productivity versus a control alga.

In another aspect the invention provides a method of producing a composition containing lipids. The methods involve performing a genetic modification to an algal organism in a gene encoding a WD40 repeat containing protein, and culturing the organism to thereby produce a composition containing lipids. The method can further involve harvesting a lipidic composition from the algal organism.

In another aspect the invention provides a method for identifying a recombinant algal organism with high lipid productivity and/or high biomass productivity. The method involves mutagenizing a population of algal organisms; screening the mutagenized algal organisms for higher lipid productivity; sequencing at least a portion of the genome of the mutagenized algal organisms; identifying genetic changes in the mutagenized organisms compared to the population of algal organisms prior to mutagenesis; recapitulating the genetic changes in a parental strain of the mutagenized algal organisms; and thereby identifying a recombinant algal organism having high lipid productivity. The method can further involve harvesting a lipidic composition from the recombinant algal organism. The recombinant algal organism with high lipid productivity and/or high biomass productivity can be any recombinant algal organism described herein. In one embodiment the recombinant algal organism can have at least 40% greater lipid productivity versus a control alga.

The summary of the invention described above is not limiting and other features and advantages of the invention will be apparent from the following detailed description of the invention, and from the claims. Section headings or sub-headings are provided solely for the convenience of the reader, and do not denote a departure from discussion or necessarily an entirely new subject matter area. Any subject matter can be discussed or disclosed under any section heading or sub-heading.

DETAILED DESCRIPTION OF THE DRAWINGS

Figure 1B:
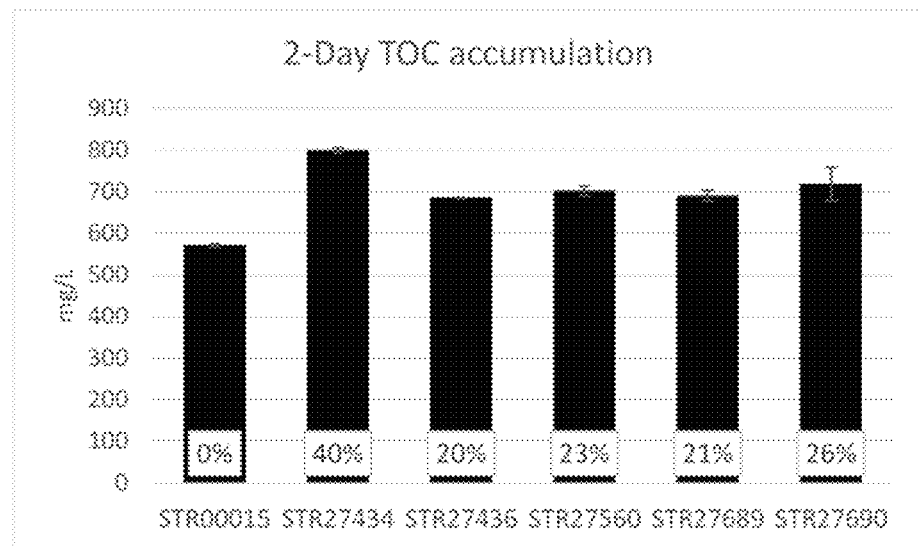
Figure 1C:
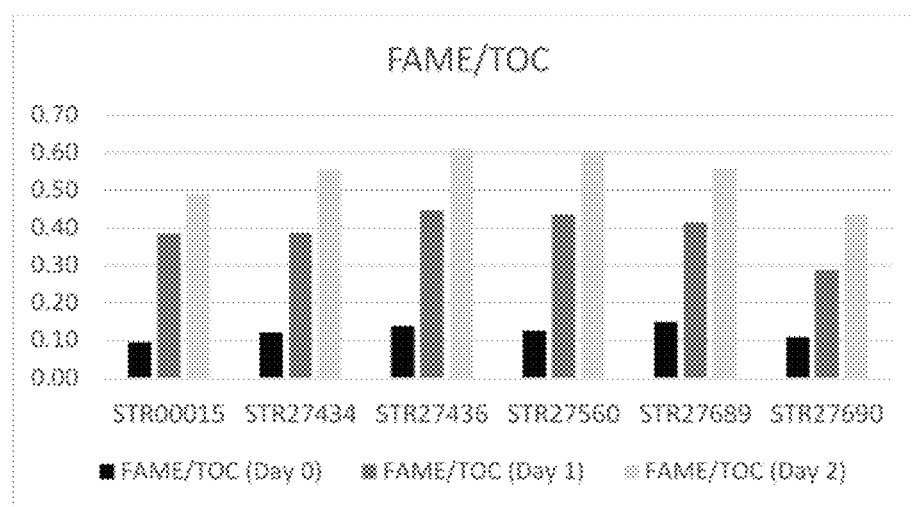

FIGS. 1A-1C are graphical illustrations of the effects on FAME and TOC accumulation in strains having a genetic modification to a nucleic acid sequence encoding a WD40 repeat family protein by mutagenesis of wild type cells (Strain 15). FIG. 1A shows 2-day FAME accumulation for various Oocystis strains. FIG. 1B shows 2-day TOC accumulation. FIG. 1C shows the ratio of FAME/TOC for various strains as an indicator of carbon partitioning. Mutagenized strains include 27434, 27436, 27550, 27689, and 27690, which all contain a deletion to SEQ ID NO: 1 (a WD40 repeat containing protein). The 2-day data was measured after 48 hours of growth in nitrogen deplete media.

Figure 2A:
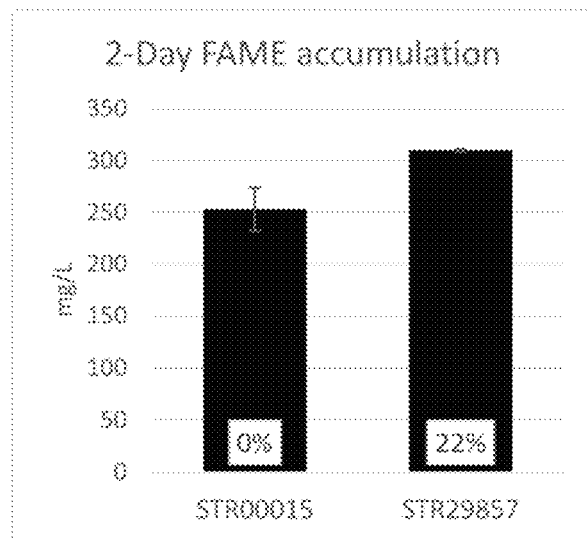
Figure 2B:
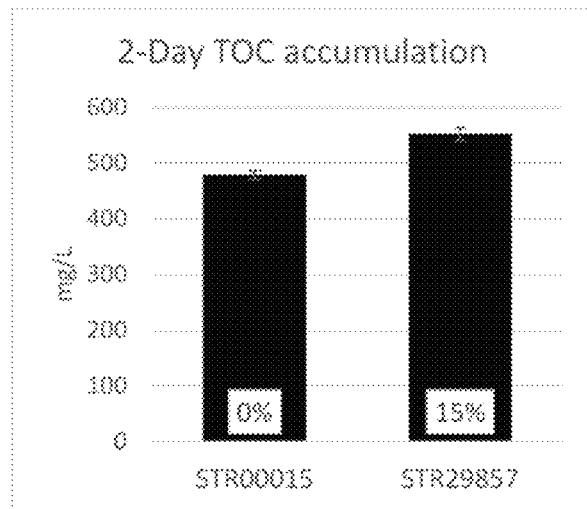
Figure 2C:
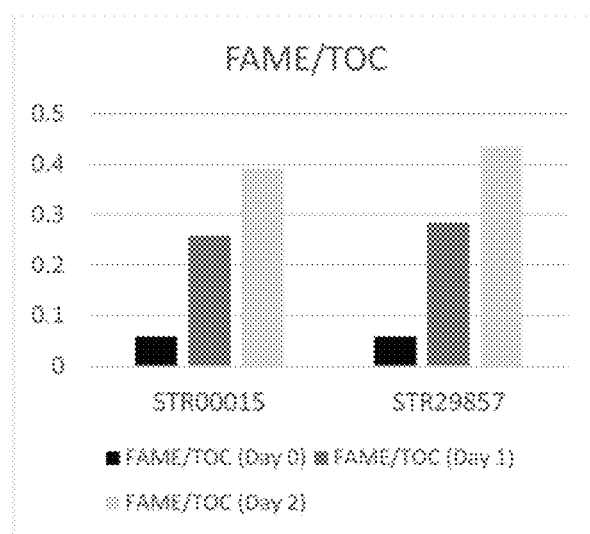

FIGS. 2A-2C are graphical illustrations of the FAME and TOC accumulation in wild type strains constructed to have a deletion of a nucleic acid sequence encoding a WD40 repeat family protein. FIG. 2A shows 2-day FAME accumulation for modified Oocystis sp. strains (29857) versus the wild type (Strain 15). FIG. 2B shows 2-day TOC accumulation. FIG. 2C shows the ratio of FAME/TOC, a useful measure of carbon partitioning.

Figure 3A:
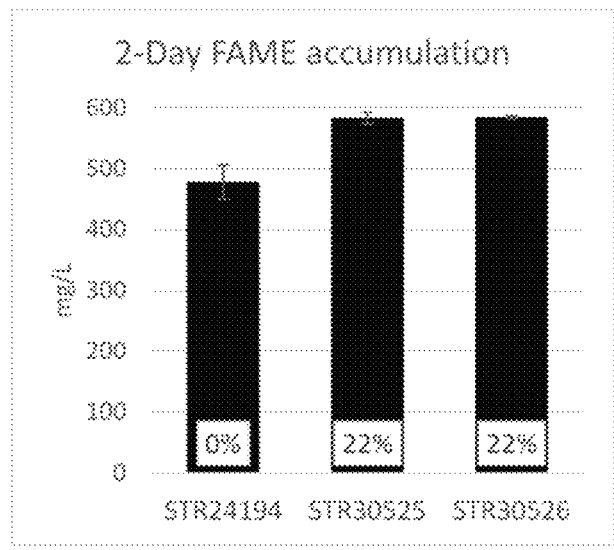
Figure 3B:
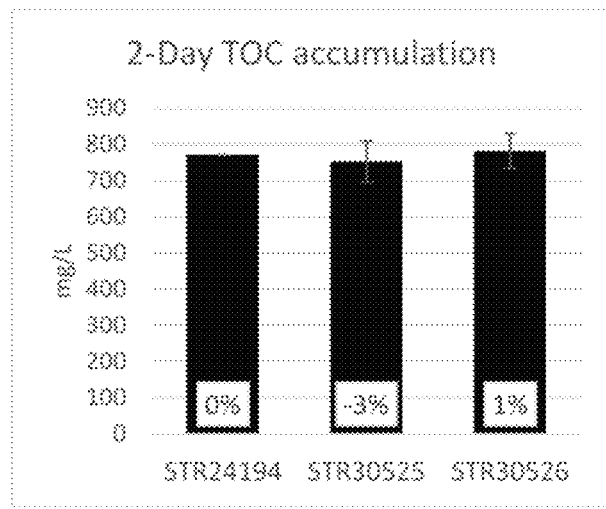
Figure 3C:
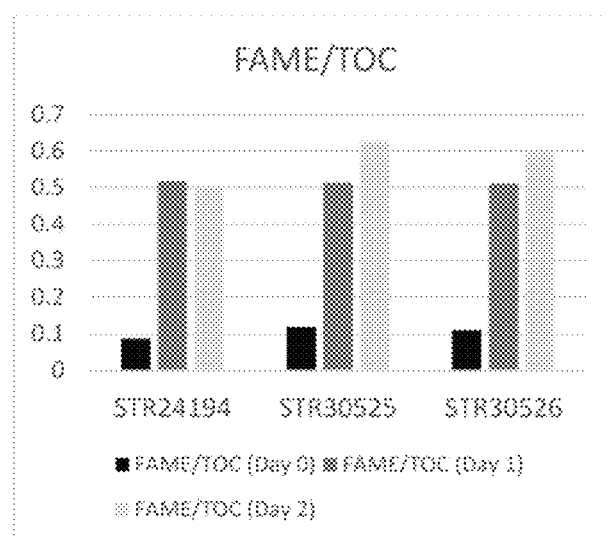

FIGS. 3A-3C are graphical illustrations of the FAME and TOC accumulation in a laboratory strain (24194) constructed to have a deletion of a nucleic acid sequence encoding a WD40 repeat family protein versus the (control) laboratory strain. FIG. 3A shows 2-day FAME accumulation for the laboratory strain (Strain 24194) and modified Oocystis sp. strains (30525 and 30526). FIG. 3B shows 2-day TOC accumulation. FIG. 3C shows the ratio of FAME/TOC, a useful measure of carbon partitioning.

Figure 4A:
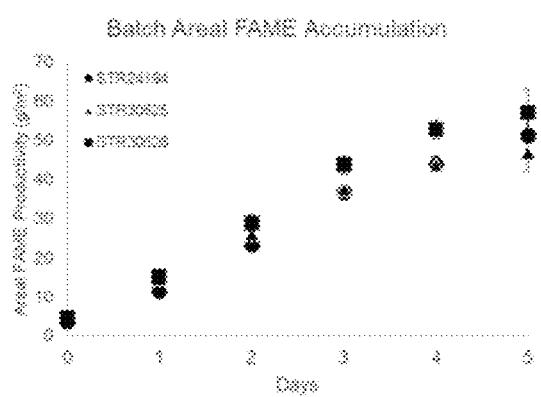
Figure 4B:
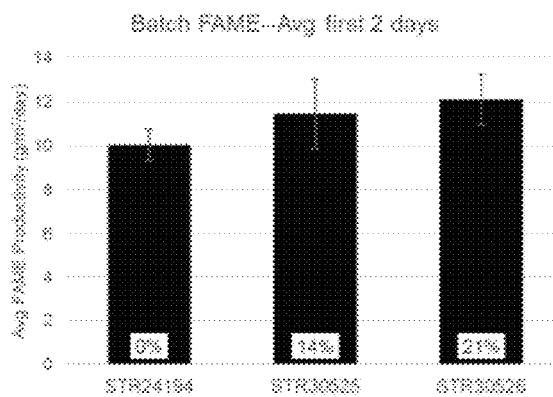
Figure 4C:
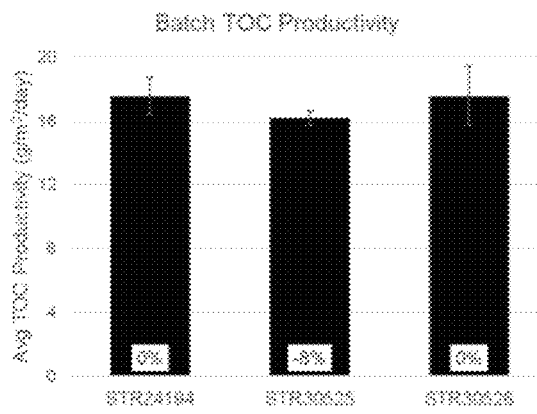
Figure 4D:
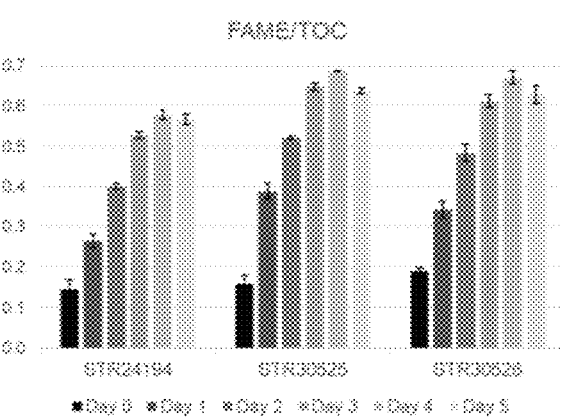

FIGS. 4A-4D provide a graphical illustration of 5-day data for FAME and TOC productivity under nitrogen deplete conditions. FIG. 4A shows areal FAME productivity v. days. FIG. 4B shows average FAME productivity for the first 2 days. FIG. 4C shows TOC productivity. And FIG. 4D shows the FAME/TOC ratios over a 5 day period.

Figure 5:
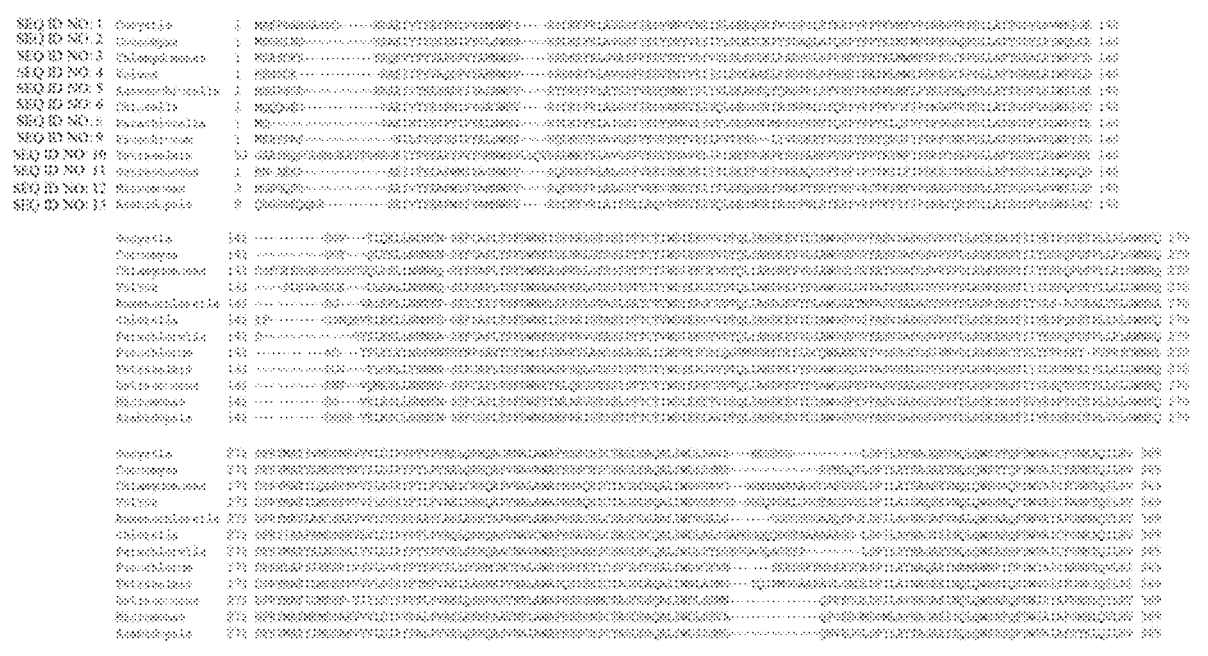

FIG. 5 is a sequence alignment of protein sequences of various Chlorophyte algae species. It is shown that there is a high degree of sequence identity across Chlorophyte species in key domains of the polypeptide sequence.

DETAILED DESCRIPTION OF THE INVENTION

The invention provides recombinant algal mutants that have a genetic modification to a nucleic acid sequence encoding a WD40 repeat containing protein. The genetic modification(s) described herein result in a recombinant or mutant cell or organism with higher lipid productivity and/or higher biomass productivity. The recombinant algal mutants can also optionally have reduced chlorophyll content and/or a reduced PSII antenna size versus a corresponding control cell or organism not having the genetic modification. In various embodiments the genetic modification(s) described herein can result in substantial increases in lipid productivity and/or biomass productivity. Any of the recombinant cells or organisms disclosed herein can be mutant photosynthetic organisms.

The recombinant cell or organism of the invention having a genetic modification described herein can have higher lipid productivity and/or higher biomass productivity than a corresponding (control) cell or organism. In some embodiments the genetic modification is an attenuation of a gene or nucleic acid sequence encoding a WD40 repeat containing protein. In any embodiment lipid productivity can be measured by FAME accumulation, and biomass productivity can be measured as the rate of biomass accumulation, for example as the total organic carbon (TOC) content of the respective cells or organisms.

In one embodiment the mutant or recombinant algal cell or organism has higher lipid and/or biomass productivity in batch culture compared to a corresponding (control) cell or organism not having the genetic modification. Batch culture is a culture where nutrients are not renewed or re-supplied to the medium during the time period the cells or organisms are cultured. In other embodiments the mutant or recombinant algal cell or organism has higher lipid and/or biomass productivity under nitrogen deplete conditions compared to a corresponding (control) cell or organism. In some embodiments the higher lipid and/or biomass productivity is achieved under batch culture and nitrogen deplete conditions; and in other embodiments the higher lipid and/or biomass productivity is achieved under semi-continuous or continuous culture conditions. Semi-continuous culture conditions are conditions where a fixed volume of culture is removed at regular time intervals and an equal volume of fresh medium is immediately added back to the culture. In various embodiments the fixed volume removed and added is from 10% to 90% of the total culture volume. Continuous culture conditions involve regular removal of culture with immediate replacement with fresh medium. Persons of ordinary skill realize that time intervals can vary with the purpose of the culture and continuous culture conditions involve a more frequent removal of culture and replacement with fresh medium than semi-continuous conditions.

Any of the mutant or recombinant cells or organisms disclosed herein can be photosynthetic cells or organisms. Any of the mutant or recombinant cells or organisms described herein can exhibit increased lipid productivity and/or increased biomass productivity under photoautotrophic conditions compared to a corresponding control cell or organism, i.e., conditions where the recombinant cells or organisms can produce their own biomass using light, carbon dioxide, water, and nutrients via photosynthesis. Corresponding (control) cells or organisms are useful for evaluating the effect of any one or more of the genetic modifications. Corresponding (control) cells or organisms do not have the one or more genetic modifications being evaluated and are subjected to the same or substantially the same conditions as the test cells or organisms such that a difference in the performance or characteristics of the cells or organisms is based only on the genetic modification(s) being evaluated. In any embodiment the corresponding (control) cells or organisms can be of the same species as the test organism. They can be derived from the same parent cell or parental line. They can also be the same or similar in every way except for the one or more genetic modification(s) being evaluated. In some embodiments the corresponding (control) cell or organism is a wild-type cell or organism. But the corresponding (control) cell or organism can also be a laboratory strain or parental strain of the test cell or organism. Substantially the same conditions can be the same conditions or slightly different conditions where the difference does not materially affect the function, activity, or expression of the nucleic acid sequence modified.

In various embodiments the recombinant cells or organisms are algal cells. In one embodiment the recombinant alga has a genetic modification to a gene encoding a WD40 repeat containing protein. The lipid products of these mutants can be further processed into biofuels or used in the production of other specialty chemical products. The gene or nucleic acid sequence encoding the WD40 repeat containing protein or domain that contains the genetic modification can encode any of the polypeptide sequences described herein, hereby disclosed in all possible combinations or sub-combinations as if set forth fully herein.

In some embodiments recombinant cells or organisms of the invention can have a reduced amount of chlorophyll b, and can have an increased chlorophyll a to chlorophyll b ratio (chl a/chl b) compared to a corresponding control cell or organism. The recombinant cells or organisms can have decreased photosynthetic antenna size, for example reduced photosystem II (PSII) and/or reduced photosystem I (PSI) antenna size. In various embodiments the cross-sectional unit size of the PSII and/or PSI antenna of the recombinant cells or organisms disclosed herein can be reduced by at least 10%, at least 20%, at least 30%, at least 25%, at least 30%, at least 35%, at least 40%, at least 45%, at least 50%, or at least 60% compared to the PSII and/or PSI antenna size of a corresponding control cell or organism.

In any embodiment the recombinant cells or organisms can have a higher growth rate and/or a higher biomass productivity than a corresponding control cell or organism not having the genetic modification, for example, higher biomass productivity per hour or per day or per period of 2 days or 3 days or 4 days or 5 days or 6 days. "Biomass" refers to cellular mass, whether of living or dead cells. Biomass productivity, or biomass accumulation, or growth rate, can be measured by any means accepted in the art, for example as ash free dry weight (AFDW), dry weight, wet weight, or total organic carbon (TOC) productivity. In any embodiment biomass productivity, or biomass accumulation, or the growth rate, can be measured as total organic carbon (TOC) productivity.

The recombinant cells or organisms of the invention can produce a greater amount of a bioproduct per time period (e.g., per minute or per hour or per day or per period of 2 days or 3 days or 4 days or 5 days or 6 days), for example a lipid product (which can optionally be measured as FAME), a fatty acid product, a carbohydrate, a protein product, or a polymer than a corresponding (control) organism not having the genetic modification(s). The amount of bioproduct can be expressed as g/time period, mg/time period, ug/time period, or any other defined quantity per defined time period described herein. Such bioproducts can be isolated from a lysate or biomass or cellular secretion of any of the recombinant cells or organisms of the invention. In some embodiments, the recombinant cells or organisms of the invention produce at least 10%, at least 15%, at least 20%, at least 25%, at least 30%, at least 35%, at least 40%, at least 45%, at least 50%, at least 60%, at least 70%, at least 80%, at least 90% or at least 100% more of a bioproduct than a corresponding control alga cultured under the substantially the same conditions, which can be batch, semi-continuous, or continuous culture conditions and may be nutrient replete culture conditions or may be nitrogen deplete conditions, and may be photoautotrophic conditions. In some embodiments the recombinant cells or organisms of the invention product at least 20% or at least 30% more lipid (e.g., as measured by FAME) over a 2-day period, or at least 30% or at least 40% more of a lipid product over a 5-day period.

Without wanting to be bound by any particular theory it is believed that the genetic modifications described herein result in an attenuation or partial or complete elimination of expression of a WD40 repeat containing protein. Such attenuation or elimination results in a significant increase in lipid productivity in the cell, which in one embodiment can be measured as the total FAME produced by the cell. A further result can be a significant increase in biomass productivity, which in one embodiment can be demonstrated by the organic carbon produced by the cell (as measured, for example, by total organic carbon).

As used herein, "exogenous" with respect to a nucleic acid or gene indicates that the nucleic acid or gene has been introduced (e.g., "transformed") into an organism, microorganism, or cell by human intervention. For example, such an exogenous nucleic acid can be introduced into a cell or organism via a recombinant nucleic acid construct. An exogenous nucleic acid can be a sequence from one species introduced into another species, i.e., a "heterologous" nucleic acid. A heterologous nucleic acid can also be an exogenous synthetic sequence not found in the species into which it is introduced. An exogenous nucleic acid can also be a sequence that is homologous to an organism (i.e., the nucleic acid sequence occurs naturally in that species or encodes a polypeptide that occurs naturally in the host species) that has been isolated and subsequently reintroduced into cells of that organism. In some embodiments an exogenous nucleic acid that includes a homologous sequence can be distinguished from the naturally-occurring sequence by the presence of non-natural sequences linked to the exogenous nucleic acid, which can include but are not limited to non-native regulatory sequences attached to the homologous gene sequence in a recombinant nucleic acid construct. Alternatively or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in Nature; 3) has been engineered using molecular biology techniques such that it lacks one or more nucleotides with respect to the naturally occurring nucleic acid molecule sequence; and/or 4) has been manipulated using molecular biology techniques such that it has one or more sequence changes or rearrangements with respect to the naturally occurring nucleic acid sequence, or has a sequence (e.g., by insertion) not found in the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the terms "transgenic" "transformed" or "recombinant" or "engineered" or "genetically engineered" refer to organisms that have been manipulated by introduction of an exogenous or recombinant nucleic acid sequence into the organism, or by genetic modification of native sequences (which are therefore then recombinant). Recombinant or genetically engineered organisms can also be organisms into which constructs for gene "knock down," deletion, attenuation, inactivation, or disruption have been introduced to perform the indicated manipulation. Such constructs include, but are not limited to, RNAi, microRNA, shRNA, antisense, and ribozyme constructs. A recombinant organism can also include those having an introduced exogenous regulatory sequence operably linked to an endogenous gene of the transgenic microorganism, which can enable transcription in the organism. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome, or can be present on a vector or other nucleic acid construct. As used herein, "recombinant microorganism" or "recombinant host cell" includes progeny or derivatives of the recombinant microorganisms of the disclosure.

Any of the recombinant algal cells or organisms described herein can be generated by human activity, for example, by classical mutagenesis and/or genetic engineering, but can also be produced by any feasible mutagenesis method, including but not limited to exposure to UV light, CRISPR/Cas9, cre/lox, gamma irradiation, or chemical mutagenesis. Screening methods can be used to identify mutants having desirable characteristics (e.g., reduced chlorophyll and increased lipid and/or biomass productivity). Methods for generating mutants of algal organisms using classical mutagenesis, genetic engineering, and phenotype or genotype screening are known in the art.

Algal Cell or Organism

The recombinant algal cell or organism of the invention can be a mutant microalga, or a mutant photosynthetic organism, or a mutant green alga. The recombinant alga can be any eukaryotic microalga such as, but not limited to, a Chlorophyte, an Ochrophyte, or a Charophyte alga. In some embodiments the mutant microalga can be a Chlorophyte alga of the taxonomic Class Chlorophyceace, or of the Class Chlorodendrophyceae, or the Class Prasinophyceace, or the Class Trebouxiophyceae, or the Class Eustigmatophyceae. In some embodiments, the mutant microalga can be a member of the Class Chlorophyceace, such as a species of any one or more of the genera *Asteromonas, Ankistrodesmus, Carteria, Chlamydomonas, Chlorococcum, Chlorogonium, Chrysosphaera, Dunaliella, Haematococcus, Monoraphidium, Neochloris, Oedogonium, Pelagomonas, Pleurococcus, Pyrobotrys, Scenedesmus,* or *Volvox*. In other embodiments the mutant microalga of the invention can be a member of the Order Chlorodendrales, or Chlorellales. In other embodiments, the mutant microalga can be a member of the Class Chlorodendrophyceae, such as a species of any one or more of the genera *Prasinocladus, Scherffelia,* or *Tetraselmis*. In further alternative embodiments, the mutant alga can be a member of the Class Prasinophyceace, optionally a species of any one or more of the genera *Ostreococcus* or *Micromonas*. Further alternatively, the mutant microalga can be a member of the Class Trebouxiophyceae, and optionally of the Order Chlorellales, and optionally a genera selected from any one or more of *Botryococcus, Chlorella, Auxenochlorella, Heveochlorella, Marinichlorella, Oocystis, Parachlorella, Pseudochlorella, Tetrachlorella, Eremosphaera, Franceia, Micractinium, Nannochloris, Picochlorum, Prototheca, Stichococcus,* or *Viridiella*, or any of all possible combinations or sub-combination of the genera. In another embodiment the recombinant alga can be a Chlorophyte alga of the Class Trebouxiophyceae and the family Coccomyxaceae, and the genus *Coccomyxa* (e.g., *Coccomyxa subellipsoidea*). Or of the family Chlamydomonadaceae and the genus *Chlamydomonas* (e.g., *Chlamydomonas reinhardtii*); or of the family Volvocaceae and the genus *Volvox* (e.g., *Volvox carteri, Volvox aureus, Volvox globator*).

In another embodiment the recombinant alga is a Chlorophyte alga of the Class Trebouxiophyceae, or Eustigmatophyceae, and can be of the Order Chlorellales or Chlorodendrales, and can be of the Family Oocystaceae, or Chlorellaceae, or Monodopsidaceae, and optionally from a genus selected from any one or more of *Oocystis, Parachlorella, Picochlorum, Nannochloropsis,* and *Tetraselmis*, in all possible combinations and sub-combinations. The recombinant alga can also be from the genus *Oocystis*, or the genus *Parachlorella*, or the genus *Picochlorum*, or the genus *Tetraselmis*, or from any of all possible combinations and sub-combinations of the genera. In one embodiment the recombinant algal cell or organism is of the Class Trebouxiophyceae, of the Order Chlorellales, and optionally of the family Oocystaceae, and optionally can be of the genus *Oocystis*.

Genetic Modification

In various embodiments the recombinant alga of the invention can have a genetic modification disclosed herein to a gene encoding a WD40 repeat containing protein. In one embodiment the recombinant alga of the invention has a genetic modification to a gene encoding a WD40 repeat containing protein or domain. In one embodiment the genetic modification is to a native or endogenous sequence of the cell or organism.

A "genetic modification" applied in the invention can be any one or more of an attenuation, a deletion, a gene "knock out," a mutation, a disruption, an insertion, insertion of a stop codon, an inactivation, a rearrangement, one or more point mutations, a frameshift mutation, a nonsense mutation, an inversion, a single nucleotide polymorphism (SNP), a truncation, a point mutation, that changes the activity or expression of the one or more gene or nucleic acids. In some embodiments the change in expression is a reduction in expression or an elimination of the expression or activity, which expression can be the production of an encoded protein. The genetic modification can be made or be present in any sequence that affects expression or activity of the gene or nucleic acid sequence, or the nature or quantity of its product, for example to a coding or non-coding sequence, a promoter, a terminator, an exon, an intron, a 3' or 5' UTR, or other regulatory sequence. A genetic modification can be performed in any structure of the gene that results in attenuation or elimination of the gene or nucleic acid product or activity. In one embodiment the genetic modification is a deletion, disruption, or inactivation. The genetic modification can be made to, or be present in, the host cell's native genome. In some embodiments, a recombinant cell or organism having attenuated expression of a gene as disclosed herein can have one or more mutations, which can be one or more nucleobase changes and/or one or more nucleobase deletions and/or one or more nucleobase insertions, into the region of a gene 5' of the transcriptional start site, such as, in non-limiting examples, within about 2 kb, within about 1.5 kb, within about 1 kb, or within about 0.5 kb of the known or putative transcriptional start site, or within about 3 kb, within about 2.5 kb, within about 2 kb, within about 1.5 kb, within about 1 kb, or within about 0.5 kb of the translational start site. The genetic modification can comprise the deletion of one or more amino acids in a polypeptide sequence of a WD40 repeat containing protein.

A frameshift mutation is a particular type of mutation that involves either insertion or deletion of bases of DNA, where the number of inserted or deleted bases is not divisible by three. As a result a frameshift mutation disrupts the natural codon reading frame. This can result in insertion of an amino acid other than the naturally occurring programmed amino acid. Some or all of the entire DNA sequence following the mutation can also be disrupted or read incorrectly, i.e., as programming an amino acid other than the naturally programmed amino acid. In some embodiments a frame shift mutation can result in premature termination of translation. Thus, in such embodiments the encoded polypeptide sequence can be much shorter, and unable to accomplish its natural function in the cell or organism. Thus, the gene or nucleic acid sequence has been functionally deleted. A nonsense mutation is the substitution of one or more base pair(s) that leads to a stop codon being inserted into a nucleic acid sequence. As a result, a nonsense mutation results in premature termination of translation, and can mean the functional deletion of the gene or nucleic acid sequence.

An "attenuation" is a genetic modification resulting in a reduction of the function, activity, or expression of a gene or nucleic acid sequence compared to a corresponding (control) cell or organism not having the genetic modification being examined, i.e., the diminished function, activity, or expression is due to the genetic modification. The activity of a nucleic acid sequence can be expression of an encoded polypeptide, a binding activity, the amount of signal transduction or transcription regulation, or other activity the nucleic acid sequence exerts within the organism. In various embodiments an attenuated gene or nucleic acid sequence disclosed herein produces less than 90%, or less than 80%, or less than 70%, or less than 50%, or less than 30%, or less than 20%, or less than 10%, or less than 5% or less than 1% of its function, activity, or expression of the gene or nucleic acid sequence compared to the corresponding (control) cell or organism. In various embodiments a gene attenuation can be achieved via a deletion, a disruption, or an inactivation. Any of the genetic modifications described herein can result in partial or complete attenuation of the function, activity, or expression of the attenuated gene or nucleic acid sequence, which in some embodiments can lead to a level of function, activity, or expression that is not substantially more than that of complete attenuation; for example, the function, activity, or expression can yield a result that is less than 10% different from a recombinant cell or organism having a complete attenuation of the gene or nucleic acid sequence.

An unmodified gene or nucleic acid sequence present naturally in the organism denotes a natural, endogenous, or wild type sequence. A deletion can mean that at least part of the object nucleic acid sequence is deleted or that at least part of the encoded product is eliminated. But a deletion can also be accomplished by disrupting a gene through, for example, the insertion of a sequence into the gene that is not naturally present (e.g., a selection marker), a combination of deletion and insertion, or mutagenesis resulting in insertion of a stop codon. But a deletion can also be performed by other genetic modifications known to those of ordinary skill that result in the loss of expression, activity, or function of a gene or nucleic acid sequence.

A functional deletion is a genetic modification that removes at least so much of the activity or expression of a gene or nucleic acid sequence so that any remaining activity or expression of the gene or nucleic acid sequence has no significant effect on the cell or organism compared to a corresponding (control) cell or organism not having the functional deletion and cultivated under the same or substantially the same conditions. In some embodiments the functional deletion can remove all function, activity, or expression of the gene or nucleic acid sequence. A functional deletion can involve an at least partial deletion of the coding or non-coding sequence of the gene. A "deletion" or "knock out" removes all function, activity, or expression of a gene or nucleic acid sequence. A "disruption" of a gene is a functional deletion by insertion or deletion of a nucleotide sequence into or from the coding, non-coding, or regulatory portion of a gene with resulting partial or complete loss of function, activity, or expression of the gene. An "inactivation" is a type of functional deletion causing partial or complete loss of activity or expression of an inactivated gene or nucleic acid sequence. An "inactivation" can be reversible or irreversible (for example the reversible or irreversible binding of a component to the gene or nucleic acid sequence). Thus, deletions, functional deletions, inactivations, and disruptions can also be attenuations; disruptions and inactivations can also be functional, i.e., can remove at least so much of the activity or expression of a gene or nucleic acid sequence so that any remaining activity or expression of the gene or nucleic acid sequence has no significant effect on the cell or organism compared to a corresponding (control) cell or organism. An attenuation can also be a downregulation of a gene or nucleic acid sequence, which refers to the cell or organism decreasing the amount of function, activity, or expression. Functional expression refers to the expression of a functional product or activity of a nucleic acid sequence. When the expressed product of a nucleic acid is a polypeptide, functional expression means expression of polypeptide activity having at least 10% or at least 25% or at least 50% or at least 75% of the activity of a corresponding (control) cell or organism not having the modification and cultivated under the same or substantially the same conditions. For activity of a gene or nucleic acid sequence functional expression means activity or expression of at least 10% or at least 25% or at least 50% or at least 75% of the activity or expression of a corresponding (control) cell or organism not having the modification at issue and cultivated under the same or substantially the same conditions. Thus, various types of genetic modifications can be given terms that overlap in description. Persons of ordinary skill know that the particular term describing a genetic modification can be dependent both on how a gene or its components, or nucleic acid sequence is being physically changed as well as on the context. The recombinant cells or organisms of the invention can have any of the types of genetic modifications described herein.

In one embodiment the genetic modification is a deletion (or "knock out") involving the introduction of a stop codon into a gene or nucleic acid sequence encoding a WD40 repeat containing protein described herein or variant thereof. For example the genetic modification can be a stop codon or frame shift mutation (or other genetic modification described herein) introduced into a gene or nucleic acid of any one of SEQ ID NO: 14-26 or a variant of any, or in a gene or nucleic acid sequence encoding any one of SEQ ID NOs: 1-13 (WD40 repeat containing proteins), or a variant of any. In one embodiment the genetic modification is a stop codon or frame shift mutation inserted into a gene or nucleic acid sequence of SEQ ID NO: 15 or 16 or a variant of either, or encoding SEQ ID NO: 1, or a variant thereof. In another embodiment the genetic modification is a stop codon or frame shift mutation inserted into a gene or nucleic acid sequence encoding SEQ ID NO: 8, or a variant thereof (WD40 repeat containing protein of *Parachlorella*). Variant sequences of any sequence described herein have at least 60% sequence identity or at least 70% sequence identity or at least 75% or at least 80% or at least 85% or at least 90% or at least 95% or at least 98% sequence identity to any nucleotide or polypeptide sequence of any of SEQ ID NOs: 1-26. In some embodiments a variant sequence can also have at least 25 or at least 50 or at least 75 or at least 100 or at least 150 or at least 200 or at least 250 or at least 300 or at least 350 or at least 400 contiguous amino acids of any one of SEQ ID NOs: 1-13, and optionally, also have a recited percent identity. In other embodiments the variants sequence can have at least 500 or at least 600 or at least 700 or at least 800 or at least 1000 or at least 1200 or at least 1400 or at least 1500 contiguous nucleotides of any sequence of SEQ ID NO: 14-26 and, optionally, also have a recited percent identity.

In one embodiment the genetic modification is a modification that results in a stop codon, nonsense mutation, or frame shift mutation (or other genetic modification described herein) at the sequence coding for SEQ ID NO: 14 (AGACTCGCACCG) (V204fs), or a variant thereof, or in SEQ ID NO: 15 or 16, or a variant of either. The genetic modification can also be targeted to a regulatory sequence with the effect of eliminating or diminishing the activity or expression of a gene or nucleic acid sequence of SEQ ID NO: 14-26 or a variant of any, or a gene or nucleic acid sequence that encodes for any one SEQ ID NO: 1-13 or a variant of any of them.

In some embodiments the genetic modification can also be a frame shift mutation, a stop codon mutation, or a nonsense mutation introduced into a gene or nucleic acid sequence (including regulatory sequences supporting such gene or nucleic acid sequences) encoding any WD40 repeat containing protein disclosed herein. In various embodiments the gene or nucleic acid sequence is of SEQ ID NO: 14-26, or a variant of any; in a specific embodiment the gene or nucleic acid sequence encodes for a polypeptide of SEQ ID NO: 1 (or a variant thereof) or a polypeptide of SEQ ID NO: 8 (or a variant thereof), which mutation can be introduced at any location of the sequence or into a regulatory sequence governing the sequence, where the modification results in a termination of transcription from the gene prior to its natural point. Thus, in one embodiment the mutation is the introduction of a frame shift mutation, stop codon, or nonsense mutation that functionally deletes or disrupts the activity or expression of the gene or nucleic acid sequence. The frame shift mutation, stop codon, or nonsense mutation (or other modification) can also be introduced at any of many different loci or locations within a gene encoding a WD40 repeat containing protein or in a regulatory sequence, for example at a promoter, terminator or other regulatory sequence, that attenuates the gene or the activity of the encoded polypeptide, and that results in functional deletion of the gene. Analogous modifications can be made to the sequence(s) for similar effect. Such insertion or deletion or other mutation can also cause a loss of expression, function or activity in the encoded WD40 repeat containing protein, and result in the effect of increased lipid productivity.

In other embodiments the genetic modification can be to a nucleic acid sequence of SEQ ID NO: 15 or 16, or to a variant of either having at least 70% sequence identity or at least 75% or at least 80% or at least 85% or at least 90% or at least 95% or at least 98% sequence identity to any nucleotide sequence of SEQ ID NOs: 15 or 16.

Any of the recombinant cells or organisms of the invention can have a reduced functional absorption cross section of PSII and/or reduced PSII antenna size. For example, the cross-sectional unit size of the PSII antenna can be reduced by at least about 10%, at least 20%, at least 30%, at least 25%, at least 30%, at least 35%, at least 40%, at least 45%, at least 50%, at least 60%, at least about 70%, or at least about 80% compared to the functional absorption cross section of PSII and/or PSII antenna size of the corresponding (control) cell or organism not having the genetic modification. In some embodiments the recombinant cells or organisms of the invention can additionally (and optionally) have a reduced functional absorption cross section of PSI or reduced PSI antenna size by the same amounts stated above versus a corresponding (control) cell or organism. All statements herein of increases in biochemical parameters (e.g., FAME productivity or TOC productivity) are versus a corresponding (control) cell or organism unless indicated otherwise.

In some embodiments, a recombinant algal cell or organism as provided herein can have increased Fv/Fm with respect to a corresponding control cell or organism. For example, the mutant photosynthetic organism may have Fv/Fm increased by at least 5%, at least 10%, at least 12%, at least 15%, at least 20%, at least 30%, at least 40% or at least 50% compared to a corresponding (control) photosynthetic organism. In various embodiments the Fv/Fm can be increased by 5-50%, or by 5-30% or by 5-20% with respect to a control photosynthetic organism.

Further, a mutant photosynthetic organism as provided herein can have an increased rate of electron transport on the acceptor side of photosystem II with respect to a control or wild type cell. The rate can be at least about 20%, 30%, 40%, 50%, 60%, 80%, or 100% higher compared to a corresponding control cell or organism. In addition, mutant photosynthetic cells or organisms of the invention can have a rate of carbon fixation (Pmax (C)) in a recombinant cell or organism as provided herein can be elevated with respect to a control organism. For example, Pmax (14 C) can be increased by at least about 20%, 30%, 40%, 50%, 60%, 80%, or 100% compared to a corresponding control cell or organism.

In some embodiments, the recombinant cells or organisms of the invention have decreased PSI and/or PSII antenna size and can optionally also have a higher amount of a ribulose bisphosphate carboxylase activase (Rubisco activase or "RA") than a corresponding (control) or wild type organism, for example, at least 1.2, 1.4, 1.6, 1.8, 2, 2.2, or 2.5 fold the amount of RA as a control organism. In some embodiments, the mutants demonstrate reduced expression of 6, 8, 10, 12, or 14 LHCP genes and increased expression of an RA gene, such as an RA-a or RA-P gene. Thus, the recombinant cells or organisms of the invention can be mutant photosynthetic organisms having reduced chlorophyll and reduced PSII antenna size where the mutants have a higher amount of Rubisco activase than control photosynthetic organisms.

The LHC super-gene family encodes the light-harvesting chlorophyll a/b-binding (LHC) proteins that constitute the antenna system of the photosynthetic apparatus. A recombinant algal mutant of the invention can also have a reduced expression of one or more LHC genes. Thus, in some embodiments the recombinant cells or organisms of the invention have at least 6, at least 8, at least 10, or at least 12 LHC genes that are attenuated or downregulated with respect to their expression level in a corresponding (control) cell or organism. In various embodiments the reduction in expression of the one or more LHC genes can be a reduction of at least 20%, or at least 30%, or at least 40%, or at least 50%, or at least 60%, or at least 70% in the level of LHC transcripts compared to the control cell or organism.

The structure of a gene consists of many elements, of which the protein coding sequence is only one part. The gene includes nucleic acid sequences that are not transcribed and sequences that are untranslated regions of the RNA. Genes also contain regulatory sequences, which includes promoters, terminators, enhancers, silencers, introns, 3' and 5' UTRs, and coding sequences, as well as other sequences known to be a part of genes. In various embodiments any of these structures or nucleic acid sequences (e.g., any of SEQ ID NO: 14-26 or variants of any) can have one or more of the genetic modifications described herein that result in the higher lipid productivity and/or higher biomass productivity as described herein.

WD40 Repeat Containing Protein

WD40 repeat containing proteins (or domains) have four or more repeating units containing a conserved core motif that ends with tryptophan-aspartic acid (WD). Proteins of this class have domain folds that form a beta propeller structure, which are symmetric folds having 4-9 anti-parallel, four-stranded beta sheets arranged radially around a central axis. The domains form a platform on which protein complexes assembly reversibly. They are believed to play a key role in the formation of protein-protein complexes. In any embodiment the genetic modification to the WD40 repeat containing protein can be to any WD40 repeat domain of the protein.

The recombinant algal cell or organism of the invention can have a genetic modification described herein to a nucleic acid sequence of any of SEQ ID NO: 14-26, or to a nucleic acid sequence having at least 60% sequence identity or at least 70% sequence identity or at least 75% or at least 80% or at least 85% or at least 90% or at least 95% or at least 98% sequence identity to any of SEQ ID NOS: 14-26. The nucleic acid sequence can encode a WD40 repeat containing protein. The genetic modification can also be to any of the disclosed sequences and also have at least 500 or at least 600 or at least 700 or at least 800 or at least 1000 or at least 1200 or at least 1400 or at least 1500 contiguous nucleotides of any sequence of SEQ ID NO: 14-26 (and, optionally, also have a recited percent identity).

The genetic modification can be to a gene or nucleic acid sequence that encodes a WD40 repeat containing protein having a polypeptide sequence of any one of SEQ ID NO: 1-13 or a variant of any of said nucleic acid sequences, and the genetic modification can result in the higher lipid productivity and/or higher biomass productivity as described herein. In various embodiments the genetic modification can be to a nucleic acid sequence that encodes a WD40 repeat containing protein (or domain) having at least 60% sequence identity or at least 70% sequence identity or at least 75% or at least 80% or at least 85% or at least 90% or at least 95% or at least 98% sequence identity to any of SEQ ID NOS: 1-13. In some embodiments the nucleic acid sequence can be a variant as stated and also encode at least 25 or at least 50 or at least 75 or at least 100 or at least 150 or at least 200 or at least 250 or at least 300 or at least 350 or at least 400 contiguous amino acids of any one of SEQ ID NOs: 1-13, or a variant of any.

In any embodiment the WD40 repeat containing protein can be a functional WD40 repeat containing protein. In various embodiments the recombinant algal cell or organism can have a genetic modification described herein to a nucleic acid sequence of SEQ ID NO: 15 or 16, or to a variant of either having at least 70%, or at least 75%, or at least 80%, or at least 85%, or at least 90%, or at least 95%, or at least 98% sequence identity.

Persons of ordinary skill know how to calculate the percent of "sequence identity" between two sequences. Any method of determining sequence identity that has acceptance by most persons of ordinary skill in the art or otherwise widely accepted in the field can be utilized to determine the sequence identity between two sequences. In one embodiment the percent of sequence identity can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad.

Sci. USA 87, 2264-2268). In one embodiment the search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx can be the BLOSUM62 matrix (Henikoff (1992), Proc. Natl. Acad. Sci. USA 89, 10915-10919). For blastn the scoring matrix can be set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Laboratory Strains

In various embodiments the one or more genetic modification(s) can be made in (i.e., derived from) a cell or organism that is a wild type, parent, or laboratory strain. Laboratory strains are cells or organisms that have been cultured in a laboratory setting. As a result of culturing over a period of time the strain has undergone some adaptation(s) advantageous to growth in the laboratory setting. A laboratory strain therefore can develop one or more advantageous characteristics from adaptations deriving from time of culturing in the laboratory environment. For example, laboratory strains can have higher biomass productivity and/or higher lipid productivity than a wild-type strain. In some embodiments one or more genetic modifications disclosed herein can be performed on a laboratory strain to result in a recombinant algal cell or organism of the invention. In such embodiments the laboratory strain can therefore be a corresponding control algal cell or organism described herein that does not have the genetic modification being considered. A test cell can be derived from the corresponding control cell or organism. For example, the corresponding control cell or organism can be a parental strain of the test cell or organism.

Increased Lipid Productivity

The recombinant mutant algae of the invention having a genetic modification to a gene or nucleic acid sequence encoding a WD40 repeat containing protein or other modification described herein can demonstrate an increase in the production of lipid in the cell or organism versus a corresponding (control) cell or organism. The increase in lipid production can be measured by any accepted and suitable method, for example using fatty acid methyl ester (FAME) analysis. In one embodiment the increase in lipid production is measured as an increase in total FAME produced by the recombinant organisms. The recombinant cells or organisms of the invention have a genetic modification to a gene or nucleic acid sequence encoding a WD repeat containing protein or domain and can exhibit at least 20% or at least 25% or at least 30% or at least 40% or at least 50% or at least 60% or at least 70% or at least 80% or at least 90% or at least 100% greater lipid productivity compared to a corresponding control cell or organism, as described herein. In other embodiments the increase in lipid productivity can be 15-25% or 15-35% or 15-45% or 15-50% or 20-25%, or 25-45%, or 25-55%, or 25-70%, or 25-90%, or 25-100%, or 25-150% or 25-200% or 30-35% or 30-45% or 30-55%. The increase can be weight for weight (w/w) of lipid. In any embodiment the lipid can be fatty acid. In one embodiment lipid productivity is measured using the FAME profile (fatty acid methyl ester) of the respective cells or organisms. In one embodiment lipid productivity can be expressed as mg/L. In other embodiments the recombinant cells or organisms of the invention can exhibit at least 50 g/m2 or at least 60 or at least 70 or at least 80 grams per square meter of FAME accumulation after 5 days of cultivation. Methods of producing a FAME profile are known to persons of ordinary skill in the art. A FAME profile can be determined using any suitable and accepted method, for example a method accepted by most persons of ordinary skill in the art. The recombinant cell or organisms of the invention can, optionally, also have an increase in biomass productivity can be 15-35% or 15-40% or 25-45% or 15-50% or 25-70% or 50-100% or 50-200% (w/w).

An increase in lipid production or lipid productivity can be measured by weight, but can also be measured in grams per square meter per day of the surface of a cultivation vessel (e.g., a flask, photobioreactor, cultivation pond). In various embodiments the recombinant cell or alga of the invention produces at least 3 or at least 4 or at least 5 or at least 6 or at least 7 or at least 8 or at least 10 or at least 12 or at least 13 or at least 14 grams per square meter per day of lipid production, which can be measured by the FAME profile. In any of the embodiments the high lipid and/or high biomass productivity phenotype can be obtained under nitrogen deplete conditions, which in some embodiments can involve dilution and/or replacement of medium with fresh nitrogen deplete medium during growth. Dilutions can be by any suitable amount, for example dilution by about 50% or by about 60% or by about 70% or at least 70%, or by about 80%, or by more than 80%, which can be done every day, every 2 days, every 3 days or every 4 days or every 5 days. In one embodiment the lipid product is a fatty acid and/or a derivative of a fatty acid. In one embodiment the fatty acids and/or derivatives of fatty acid comprise one or more species of molecules having a carbon chain between C8-C12, and/or C8-C18 and/or C8-C20 and/or C8-C22 and/or C8-C24, hereby disclosed in all possible combinations and sub-combinations. In one embodiment the growth conditions can be batch growth, involving spinning cells to remove nitrogen from the medium, replacing with nitrogen deplete medium, and resuming batch growth.

In any of the embodiments the genetic modification to the gene or nucleic acid sequence encoding a WD repeat containing protein can result in an attenuation of expression of the respective genes. The genetic modification of any one or more of these genes or nucleic acids can be any of those described herein, e.g., any one or more of SEQ ID NOs: 14-26. In one embodiment the genetic modification is a deletion, disruption, or inactivation. In another embodiment the genetic modification is a deletion (which optionally, can be a functional deletion) or a disruption of the gene.

Biomass Productivity

The recombinant algal cells of the invention having a genetic modification to a gene or nucleic acid sequence encoding a WD40 repeat containing protein described herein, and can also have higher biomass productivity than a corresponding (control) organism not having the genetic modification. Biomass can be measured as an increase in the total organic carbon (TOC) produced by the cell or organism, for example measured by TOC analysis known to persons of ordinary skill in the art. The recombinant cells can have at least 12% higher, or at least 15% higher, or at least 20% higher or at least 25% higher or at least 30% higher or at least 35% higher, or at least 50% higher or at least 60% higher or at least 70% higher or at least 80% higher or at least 90% higher or at least 100% higher or at least 125% higher or at least 150% higher biomass productivity than a corresponding (control) cell or organism, which can be measured by total organic carbon analysis. In other embodiments the biomass productivity can be 10-15% higher or 15-25% higher or 20-25% higher or 20-30% higher or 20-40% higher or 20-45% higher. The increase in biomass productivity can, optionally, be in addition to the increase in lipid productivity.

Various methods of measuring total organic carbon are known to persons of ordinary skill in the art. Biomass productivity can be measured as mg/ml of culture per time period (e.g., 1 day or 2 days or 3 days or 4 days or 5 days). In some embodiments the higher biomass productivity and/or higher lipid productivity as described herein can occur under nitrogen deplete conditions. Thus, in one embodiment the recombinant alga or cell of the invention can have higher lipid production and/or higher total organic carbon production than a corresponding (control) cell or organism, which higher amount can be produced under nitrogen deplete or low nitrogen conditions. Nitrogen deplete conditions can involve culturing in a buffer having less than 0.5 mM of nitrogen in any available form external to the cell or organism. In some embodiments the cells can be cultured in 0.5 mM or less of KNO3 or urea as a nitrogen source. Other buffers may also be used and be nitrogen deplete [[if they contain a level of nitrogen that does not change the physiology of a nitrogen-related parameter (e.g., lipid productivity or biomass productivity) by more than 10% versus culturing the cell in a medium free of a nitrogen source external to the cells or organisms.]] In any embodiment biomass productivity can be evaluated by measuring an increase in the total organic carbon of the cells. Nutrient replete conditions are those where the growth of the cultivated organism is not limited by a lack of any nutrient. A nitrogen free medium is also considered nitrogen deplete conditions.

Methods of Producing Lipid

The invention also provides methods for producing a lipid containing product. The methods involve culturing a recombinant algal cell or organism described herein to thereby produce a lipid product. Any of the methods can also involve a step of harvesting lipid produced by the recombinant algal cell or organism described herein. The culturing can be for a suitable period of time, for example, at least 1 day or at least 3 days or at least 5 days.

The invention also provides methods for producing a composition containing lipids. In one embodiment the methods can involve performing a genetic modification to an algal organism in a gene or nucleic acid sequence encoding a WD40 repeat containing protein. The methods can also involve a step of culturing a recombinant algal cell or organism described herein to thereby produce a composition containing lipids. The composition can be a biomass composition or biomass product containing any one or more recombinant algae described herein. The cultivating can be done in any suitable medium conducive to algal growth (e.g., an algal growth medium or any medium described herein). The methods can also involve a step of harvesting lipids from the composition or biomass containing lipids. The methods can involve a step of harvesting lipids from the recombinant cells or organisms. Any of the methods herein can also involve a step of purifying the lipid containing composition to produce a biofuel or biofuel precursor. A biofuel precursor is a composition containing lipid molecules that can be purified or otherwise converted into a biofuel.

The invention also provides methods of producing a recombinant algal cell or organism having higher lipid productivity and/or higher biomass productivity than a corresponding control cell or organism. The methods involve exposing algal cells or organisms to ultraviolet light to produce a recombinant cell or organism described herein that has higher lipid productivity than a corresponding control cell or organism. In one embodiment algal organisms having higher lipid productivity can be identified by contacting the recombinant cells with a stain that identifies lipids (e.g., by BODIPY dye). Optionally methods can include a step of isolating lipids from the recombinant algal organisms. Organisms having higher biomass productivity can be identified by TOC analysis. The recombinant alga can be cultivated in any suitable growth media for algae, such as any of those described herein. The uv treatment can involve, for example, subjecting the culture to uv light, or gamma radiation, or both, for a suitable period of time or under a suitable uv regimen or gamma radiation regimen. Persons of ordinary skill understand suitable regimens for uv exposure for mutagenesis. The uv regimen can involve exposing the cells or organisms to uv radiation, which can be performed in batches with each batch receiving a dose. Multiple cell batches can receive different doses of energy for each batch of cells. Subjecting the algal organism to ultra-violet light can comprise exposing the cell or organism to at least 10 or at least 15 uJ/cm2 of energy, which exposure can be performed within 1 second or within 5 seconds or within 30 seconds or within 1 minute. In some embodiments 4 or 5 batches of cells can receive doses of exposure to 16-57 uJ/cm2 of energy, and exposure energy can increase with each separate batch. The cell batches can be pooled together after exposures are complete. The recombinant alga (or pooled algae) can be cultivated for at least 2 days or at least 3 days, or at least 4 days, or at least 5 days, or at least 6 days, or at least 10 days, or at least 20 days, or from 2-10 days, or from 2-20 days or from 2-25 days after exposure. The recombinant algal organisms can be any described herein. The uv regimen can involve exposing the cells or organisms to multiple exposures to uv radiation, which can become progressively stronger.

Any of the recombinant cells or organisms of the invention can be cultivated in batch, semi-continuous, or continuous culture to produce the higher biomass productivity and/or higher lipid productivity. In some embodiments the culture medium can be nutrient replete, or nitrogen deplete (—N). In some embodiment the culturing is under photoautotrophic conditions, and under these conditions inorganic carbon (e.g., carbon dioxide or carbonate) can be the sole or substantially the sole carbon source in the culture medium.

The invention also provides a biofuel comprising a lipid product of any of the recombinant cells or organisms described herein. The biofuel is produced by purifying a lipid containing composition produced by a recombinant algal cell or organism described herein. The biofuel can be produced by purifying or otherwise converting a lipid product produced by a recombinant algal cell or organism described herein to produce a biofuel. In one embodiment the biofuel is a biodiesel fuel, which can contain fatty acid methyl ester molecules in sufficient proportion to be combustible in an internal combustion engine. In various embodiments the biofuel can contain carbon chains with an average carbon chain length of at least 5 carbon atoms, or at least 8 carbon atoms, or at least 10 carbon atoms.

FAME and TOC Analysis Methods

The lipid productivity of the cells or organisms can be measured by any method accepted in the art, for example as an increase or decrease in fatty acid methyl esters comprised in the cell, i.e., FAME analysis. In various embodiments any of the recombinant algal cells or organisms of the invention can have higher biomass productivity as described herein versus corresponding control cells or organisms. In some embodiments the recombinant algal cells or organisms of the invention can have higher lipid productivity and also higher biomass productivity compared to a corresponding control cell or organism. Biomass productivity can be measured by any methods accepted in the art, for example by measuring the total organic carbon (TOC) content of a cell. Embodiments of both methods are provided in the Examples.

"FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. In some embodiments lipid productivity is assessed as FAME productivity in milligrams per liter (mg/L), and for algae, may be reported as grams per square meter per day (g/m2/day). In semi-continuous assays, mg/L values are converted to g/m2/day by taking into account the area of incident irradiance (the SCPA flask rack aperture of 1½ inches×3⅜", or 0.003145 m2) and the volume of the culture (550 ml). To obtain productivity values in g/m2/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise. The term "fatty acid product" includes free fatty acids, mono-di, or tri-glycerides, fatty aldehydes, fatty alcohols, fatty acid esters (including, but not limited to, wax esters); and hydrocarbons, including, but not limited to, alkanes and alkenes).

Embodiments

In one embodiment the invention provides a recombinant algal organism of the Class Trebouxiophyceae having a genetic modification in a gene or nucleic acid sequence encoding a WD40 repeat containing protein. The recombinant alga exhibits higher lipid productivity and/or biomass productivity versus a corresponding control algal cell not having the genetic modification. In various embodiment the Trebouxiophyceae organism can be from the family Oocystaceae or Chlorellaceae. In one embodiment the organism is of the genus *Oocystis*.

In one embodiment the invention provides a recombinant Trebouxiophyceae organism having a deletion, disruption, or inactivation in a gene or nucleic acid sequence encoding a WD40 repeat containing protein. The deletion can be a functional deletion. In one embodiment the deletion, disruption, or inactivation involves the insertion of a nonsense mutation or a frameshift mutation in a gene or nucleic acid sequence encoding a WD40 repeat containing protein. In one embodiment the encoded WD40 repeat containing protein can have at least 80% or at least 85% or at least 90% or at least 95% sequence identity to SEQ ID NO: 1 or 8. In another embodiment the recombinant cell or organism can have the deletion, disruption, or inactivation in a nucleic acid sequence encoding a WD40 repeat containing protein, which be a nucleic acid having at least 80% or at least 90% or at least 95% sequence identity to SEQ ID NO: 15 or SEQ ID NO: 16. The recombinant alga exhibits higher lipid productivity and/or biomass productivity versus a corresponding control algal cell not having the genetic modification. The alga can be a Trebouxiophyceae organism, for example from the family Oocystaceae, and optionally from the genus *Oocystis*. The increase in lipid productivity can be an increase in 2-day FAME accumulation of at least 20% w/w, or at least 25%, or 30-50% or 30-55%, which can, optionally, be cultivated under nitrogen deplete conditions. The recombinant cells or organisms can, optionally, also have an increase in biomass productivity of at least 12% or at least 15% or at least 20% or 15-25% or 20-40%, which can be expressed as 2-day TOC accumulation. Thus in one embodiment the recombinant cells or organisms have an increase in lipid productivity (as measured by FAME profile) of 30-55% and an increase in biomass productivity of at least 20% versus a control cell or organism. In another embodiment the increase in lipid productivity can be 20-40%. The increase in FAME accumulation and/or TOC accumulation can be measured after two days or after five days cultivation, and can be in nitrogen deplete conditions. The recombinant cells or organisms can also have a FAME/TOC ratio of greater than 0.3 after 2 days of cultivation.

In another embodiment the cells or organisms of the invention can have an increase in lipid productivity of at least 20% (as measured by 2-day FAME accumulation) and, optionally, an increase in biomass productivity of at least 12% (as measured by TOC); and optionally also have a FAME/TOC ratio of greater than 0.3 or 0.4. In another embodiment the cells or organisms of the invention can have an increase in lipid productivity of at least 20% (as measured by 2-day FAME accumulation); and optionally also have a FAME/TOC ratio of greater than 0.5.

In one embodiment the invention provides a recombinant algal organism of the Class Trebouxiophyceae having a genetic modification to a gene or nucleic acid sequence encoding a WD40 repeat containing protein. In one embodiment the gene or nucleic acid sequence is any one of SEQ ID NO: 14-26 or a variant of any, or can be a gene or nucleic acid sequence encoding any one of SEQ ID NO: 1-13, or a variant of any. The genetic modification can be a deletion (optionally a functional deletion) or disruption of the gene or nucleic acid sequence. The deletion can be a functional deletion. The recombinant alga exhibits higher lipid productivity and, optionally, higher biomass productivity versus a corresponding control algal cell not having the genetic modification. In various embodiment the Trebouxiophyceae organism can be from the family Oocystaceae or Chlorellaceae. In one embodiment the organism is of the genus *Oocystis*. The increase in lipid productivity can be an increase in 2-day or 5-day FAME accumulation of at least 20% w/w, or 30-50% or 30-55%, which can, optionally, be cultivated under nitrogen deplete conditions. The recombinant cells or organisms can, optionally, also have an increase in biomass productivity of at least 15% or at least 20% or 15-25% or 20-40%, which can be expressed as 2-day or 5-day TOC accumulation. Thus in one embodiment the recombinant cells or organisms have an increase in lipid productivity of 30-55% and an increase in biomass productivity of at least 20%. In another embodiment the increase in lipid productivity can be 20-40%. The increase in FAME accumulation and/or TOC accumulation can be measured after two days or after five days cultivation in nitrogen deplete conditions. In another embodiment the cells or organisms of the invention can have an increase in lipid productivity of at least 50% (as measured by 5-day FAME accumulation); and optionally also have a FAME/TOC ratio of greater than 0.5 or 0.6 after 5 days cultivation.

EXAMPLE 1

Various aliquots of 10 mL of Strain 15 (STR00015 or "wild type") Oocystis sp. were acclimated to diel growth conditions on urea supplemented minimal media. Different aliquots of cells at a concentration of $2 \times 10^6$ cells/mL were then exposed to different amounts of UV radiation (22.4, 33.6, 44.8 and 56 $mJ/cm^2$ using at total of 50, 50, 50 and 20 mL of culture, respectively) in a UV crosslinker apparatus. The mutagenized cell aliquots were allowed to recover in the dark for 48 hrs. Cultures were then scaled up in low light (~100 uE) before a first round of enrichment. The mutagenized cells were then acclimated to diel growth at a light intensity of ~100 uE and 1% $CO_2$ in urea supplemented minimal medium for a week. The cultures were scaled up for 3 days, bubbled with 1% $CO_2$ at a maximum irradiance of ~1400 uE under diel conditions, to an OD730 of about 1.0. The cultures was then centrifuged at 5000 g for 10 mins and the cell pellets resuspended in nitrogen-free minimal medium to an OD730 of about 0.9. This nitrogen-free culture was then incubated for 48 hrs in square-bottom flasks bubbled with 1% $CO_2$ at a maximum irradiance of about 1400 uE under diel conditions. After 48 hours in nitrogen-free batch growth, an aliquot of cells was removed and subjected to staining with the lipid specific dye BODIPY for 10 mins in the dark at a final concentration of 0.2 ug/mL.

Mutant cells having the highest level of BODIPY staining were enriched by fluorescence activated cell sorting (FACS). Enriched cell populations were scaled up and starved for nitrogen as described above, and then subjected to additional rounds of BODIPY-based FACS enrichment. This iterative process was repeated for a total of five rounds, with the top 2%, 1%, 1%, 0.25% and 0.25% of the population retained in each iteration.

The final sort was plated on minimal medium agar plates supplemented with urea to isolate single axenic colonies.

Isolates were scaled up in T25 tissue culture flasks in minimal medium supplemented with urea, then transitioned to nitrogen-free minimal medium for 48 hrs. The lipid and biomass accumulation of isolated mutants were compared to the parental strain STR00015, with lipid content measured by total fatty acid methyl ester (FAME) analysis and biomass measured by total organic carbon (TOC). As can be seen in FIG. 1, several isolates from the screen showed an increase in accumulated FAME and TOC, as well as FAME/TOC—an indicator of how much fixed carbon is partitioned to lipids. This indicated that mutants with improved lipid productivity had been isolated by the process described. Strain 27434 was identified as having high FAME and biomass accumulation.

EXAMPLE 2

Genomic DNA was isolated from Strain 27434 along with parental (wild type) Strain 15 and sequenced on high throughput sequencing system generating 150 bp paired end reads. Reads were processed, mapped to the wild type strain as reference genome and analyzed by a small variants algorithm. An example of a small variants algorithm is the Freebayes polymorphism detection software, although other programs can also be successfully utilized. Analysis of SNPs and small insertions/deletions (InDels) revealed Strain '434 contained a total of 170 polymorphisms. Twenty-four of these mutations were located within exons or at splice junctions and were prioritized for Cas9-mediated gene deletion as they had the highest probability of altering gene function and/or activity, as shown in Table 1 below.

TABLE 1

Mutations identified within exons or at splice junctions in Strain '434

| | Transcripts | Descriptions | Type | Ref | Alt | AAMod |
|---|---|---|---|---|---|---|
| 1 | 3EUKT2015873 | Protein kinase-like (PK-like) | SNP | G | A | Gln1301* |
| 2 | 3EUKT2027500 | YVTN repeat-like/Quinoprotein amine dehydrogenase | Deletion | AGACTCGCACCG | AG | Val204fs |
| 3 | 3EUKT2031181 | CAAX amino terminal protease self-immunity | SNP | G | A | Gln48* |
| 4 | 3EUKT2028953 | Proteasome subunit alpha type-1-A | SNP | C | T | Leu546Phe |
| 5 | 3EUKT2014620 | 3-methylcrotonyl-CoA carboxylase alpha subunit | SNP | C | A | Ala426Ser |
| 6 | 3EUKT2012690 | DNA-directed DNA polymerase family protein | SNP | G | A | Ala627Val |
| 7 | 3EUKT2036647 | Conserved predicted protein | SNP | C | T | Glu640Lys |
| 8 | 3EUKT2016841 | Conserved predicted protein | SNP | T | A | Leu332Gln |
| 9 | 3EUKT2025932 | Chitin binding Peritrophin-A domain | SNP | C | T | Pro239Leu |
| 10 | 3EUKT3238737 | Retrovirus-related Pol polyprotein from transposon 17.6 | SNP | G | A | Ser895Phe |
| 11 | 3EUKT2017815 | Phosphoglycerate mutase-like protein | Complex | CC | TT | Gly235Glu |
| 12 | 3EUKT2020372 | Conserved predicted protein | SNP | A | G | Thr118Ala |
| 13 | 3EUKT2011248 | RAP domain | SNP | G | A | Gly1722Asp |
| 14 | 3EUKT2015114 | Conserved predicted protein | SNP | G | A | Arg576His |
| 15 | 3EUKT2013326 | Manganese-dependent ADP-ribose/CDP-alcohol diphosphatase | SNP | G | A | Ser174Phe |
| 16 | 3EUKT2015233 | Phosphatidylinositol (PI) phosphodiesterase | SNP | C | T | Ser106Phe |
| 17 | 3EUKT2015577 | T-complex 1 subunit beta | SNP | G | A | Glu265Lys |
| 18 | 3EUKT2015261 | Cell surface protein homologous to bacterial outer membrane proteins | SNP | C | T | Pro171Ser |
| 19 | 3EUKT2026772 | Conserved predicted protein | SNP | G | A | Pro18Ser |
| 20 | 3EUKT2021194 | Conserved predicted protein | SNP | C | T | Pro48Leu |
| 21 | 3EUKT2021524 | Conserved predicted protein | SNP | C | T | Ser19Leu |

TABLE 1-continued

Mutations identified within exons or at splice junctions in Strain '434

| Transcripts | Descriptions | Type | Ref | Alt | AAMod |
|---|---|---|---|---|---|
| 22 3EUKT2018868 | Conserved predicted protein | SNP | T | A | Asn84Ile |
| 23 3EUKT2022105 | Axonemal inner arm dynein heavy chain 4 | SNP | G | A | Ala202Val |
| 24 3EUKT2018529 | Ribonuclease Inhibitor | SNP | G | A | Splice junction |

The remaining 146 mutations were either intergenic or present in introns of a gene. An assessment of transcriptomics data from Strain 15 (wt) and Strain 27434 indicated that none of these 146 mutations had any significant impact on gene expression or transcript splicing.

EXAMPLE 3

Identification of Mutations

To identify which mutation(s) caused the high lipid phenotype in Strain 27434, independent knockouts of genes bearing SNPs in the strain (Table 1) were conducted via RNP-based Cas9-mediated gene disruption in two background strains: (i) the Strain 15 wild type parental strain; and (ii) Strain 24194—a laboratory strain evolved from Strain 15 and having improved biomass and lipid productivity.

All the strains generated were tested for improved biomass and lipid accumulation during nitrogen starvation in T25 flasks. From this analysis three independent lines were identified having a deletion of 3EUKT2027500, a gene encoding a WD40 repeat containing protein. These lines showed significantly higher biomass and lipid accumulation compared to the parental lines. One of these was constructed in the Strain 15 (wt) control strain (FIG. 2), while the other two were constructed in the Strain 24194 control strain (FIG. 3). As shown in FIG. 2, the first genetically engineered strain (identified as Strain 29857) showed a 22% and 15% improvement in accumulated FAME and TOC, respectively, compared to Strain 15. The strains engineered in the Strain 24194 control (identified as Strains 30525 and 30526) showed a 22% increase in FAME accumulation (FIG. 3).

EXAMPLE 4

Large scale productivity testing in 500 mL square-bottom flasks was conducted as described above, but over a 5 day period. The study revealed that the two knockout lines in laboratory Strain 24194 (Strain 30525 and 30526) showed a 14% and 21% improvement in lipid productivity, respectively (FIG. 4), confirming the results in the T25 flasks. The measured FAME/TOC was also substantially higher on each day of the experiment for both engineered strains (FIG. 4). The data therefore showed that deletion of 3EUKT2027500 provides a substantial increase in carbon partitioning and lipid productivity.

EXAMPLE 5

The amino acid sequence of 3EUKT2027500 (#2 in Table 1) was analyzed for functional domains and orthologs in other species. 3EUKT2027500 encodes a WD40 repeat containing protein with four tandem domains with weak similarity to WD40 repeats. WD40 repeats are short minimally conserved structural motifs of about 40 amino acids often beginning with a glycine-histidine (GH) dipeptide and ending with tryptophan-aspartic acid (WD) dipeptide. Multiple copies of these repeats fold together to form the WD40 domain, which functions as a scaffold enabling interaction with proteins and nucleic acid and facilitating the formation of multiprotein complexes. WD40 repeat containing proteins are involved in a variety of cellular processes, including cell cycle progression, transcriptional regulation, signal transduction, apoptosis, biosynthesis of plant cell walls, anthocyanin biosynthesis, etc.

Further sequence identity analysis summarized in Table 2 revealed orthologs of 3EUKT2027500 are highly conserved and broadly distributed in green algae and plants.

TABLE 2

Alignment of Entire Protein Sequences of 3EUKT2027500 Orthologs

| | Organisms | Gene/Seq ID | % Identity | % Similarity [Positives] |
|---|---|---|---|---|
| 1 | Coccomyxa subellipsoidea | XP_005642574.1 SEQ ID NO: 2 | 78 | 89 |
| 2 | Chlamydomonas reinhardtii | Cre16.g674000 SEQ ID NO: 3 | 69 | 78 |
| 3 | Volvox carteri | XP_002950453.1 SEQ ID NO: 4 | 72 | 80 |
| 4 | Auxenochlorella protothecoides | RMZ56784.1 SEQ ID NO: 5 | 62 | 76 |
| 5 | Chlorella sorokiniana | PRW57951.1 SEQ ID NO: 6 | 70 | 81 |
| 6 | Chlorella variabilis | XP_005847572.1 SEQ ID NO: 7 | 69 | 80 |
| 7 | Parachlorella sp WT1185 | 3EUKT595038 SEQ ID NO: 8 | 73 | 85 |
| 8 | Picochlorum celeri | 3EUKT2133049 SEQ ID NO: 9 | 44 | 62 |
| 9 | Tetraselmis | 3EUKT668672 SEQ ID NO: 10 | 73 | 82 |
| 10 | Ostreococcus lucimarinus | XP_001417471.1 SEQ ID NO: 11 | 71 | 86 |
| 11 | Micromonas commoda | XP_002507884.1 SEQ ID NO: 12 | 72 | 87 |
| 12 | Arabidopsis | AT1G12910 SEQ ID NO: 13 | 70 | 83 |

An alignment study of the protein sequences from the Table 2 orthologs was conducted and showed a high degree of sequence conservation across Chlorophyte algae species and across the entire length of the proteins, and particularly in key domains as illustrated in FIG. 5. Sequence similarity was calculated using the bioinformatics matrix BLOSUM62 for sequence alignment.

It will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Other embodiments are within the following claims.

What is claimed is:

1. A method of producing a composition containing lipids comprising,
performing a deletion, disruption, or inactivation in an algal organism in a nucleic acid sequence having at least 90% sequence identity to SEQ ID NO: 15 and encoding a WD40 repeat containing protein having at least 90% sequence identity to the polypeptide of SEQ ID NO: 1 to produce a recombinant algal organism;
culturing the product recombinant algal organism in a culture medium, and thereby producing a composition containing lipids,
wherein the recombinant algal organism has higher lipid and/or higher biomass productivity versus a corresponding control algal host cell not having the deletion, disruption, or inactivation of the nucleic acid comprising the nucleotide sequence having at least 90% sequence identity to SEQ ID NO: 15 and encoding a WD40 repeat containing protein having at least 90% sequence identity to the polypeptide of SEQ ID NO: 1.

2. The method of claim 1 further comprising harvesting the composition containing lipids from the recombinant algal organism.

3. The method of claim 1 wherein the recombinant algal organism has at least 30% greater lipid productivity versus a control alga that does not have the deletion, disruption, or inactivation.

4. The method of claim 1 wherein the recombinant alga exhibits at least 40 grams per square meter per day of lipid production after 5 days of cultivation.

5. The method of claim 1 wherein the deletion, disruption, or inactivation is a frame shift mutation.

6. The method of claim 1 wherein the deletion, disruption, or inactivation is a knock out mutation.

7. The method of claim 1 wherein the deletion, disruption, or inactivation is performed by mutagenesis.

8. The method of claim 1 wherein the culturing is performed under nitrogen deficient conditions.

9. The method of claim 1 wherein the recombinant alga has higher biomass productivity per unit time as measured by production of total organic carbon (TOC) versus a control alga that does not comprise the deletion, disruption, or inactivation.

10. The method of claim 9 wherein the recombinant alga has at least 15% higher biomass productivity.

11. The method of claim 1 wherein the algal organism is a Chlorophyte alga.

12. The method of claim 11 wherein the Chlorophyte alga is of the class Trebouxiophyte.

13. The method of claim 12 wherein the recombinant algal organism is an alga of the genus *Oocystis*.

14. The method of claim 1 further comprising:
mutagenizing a population of the algal organisms to perform the deletion, disruption, or inactivation in an algal organism in a nucleic acid sequence having at least 90% sequence identity to SEQ ID NO: 15 and encoding a WD40 repeat containing protein having at least 90% sequence identity to the polypeptide of SEQ ID NO: 1;
screening the mutagenized algal organisms for higher lipid productivity;
sequencing at least a portion of the genome of the mutagenized algal organisms;
identifying the deletion, disruption, or inactivation in the gene encoding a WD40 repeat family protein compared to the population of algal organisms prior to mutagenesis; and
recapitulating the deletion, disruption, or inactivation in a parental strain of the mutagenized algal organisms to produce the product recombinant algal organism.

15. The method of claim 14 further comprising harvesting a lipidic composition from the algal organism.

16. The method of claim 14 wherein the algal organism is a Chlorophyte alga.

17. The method of claim 14 wherein the Chlorophyte alga is of the class Trebouxiophyte.

18. The method of claim 17 wherein the recombinant algal organism is an alga of the genus *Oocystis*.

* * * * *